United States Patent [19]

Zimmerman

[11] Patent Number: 4,836,846

[45] Date of Patent: Jun. 6, 1989

[54] HERBICIDAL INDOLE SULFONAMIDES

[75] Inventor: Donna F. Zimmerman, Landenberg, Pa.

[73] Assignee: E. I. Du Pont de Nemours and Company, Wilmington, Del.

[21] Appl. No.: 179,558

[22] Filed: Apr. 8, 1988

Related U.S. Application Data

[60] Division of Ser. No. 911,420, Sep. 25, 1986, Pat. No. 4,764,610, which is a continuation of Ser. No. 671,071, Nov. 13, 1984, abandoned, which is a continuation of Ser. No. 382,876, Jun. 1, 1982, abandoned, which is a continuation-in-part of Ser. No. 283,928, Jul. 16, 1981, abandoned.

[51] Int. Cl.$^4$ .................. C07D 403/12; A01N 43/70; A01N 43/66
[52] U.S. Cl. ...................... 71/93; 544/212; 544/219; 544/207; 544/209
[58] Field of Search .................. 71/93; 544/212, 219, 544/207, 209

[56] References Cited

U.S. PATENT DOCUMENTS

| | | | |
|---|---|---|---|
| 4,127,405 | 11/1978 | Levitt | 71/93 |
| 4,339,266 | 7/1982 | Levitt | 71/92 |
| 4,368,067 | 1/1983 | Budzinski et al. | 71/92 |
| 4,391,627 | 7/1983 | Levitt | 71/90 |

FOREIGN PATENT DOCUMENTS

| | | | |
|---|---|---|---|
| 747920 | 12/1966 | Canada | 260/320 |
| 1468747 | 1/1967 | France . | |
| 121788 | 5/1964 | Netherlands . | |

OTHER PUBLICATIONS

Logemann et al., Chem. Ab., 53, 18052g, (1959).
Wojciechowski, J. Acta. Polon. Pharm., 19, pp. 121–125, (1962), (Chem. Ab., 59, 1633e).
Ouf et al., Chemical Abstracts entry, 84:17048d.
"Thiophenesulfonylureas Structurally Related to Antidiabetic Drugs," (*Chemical Abstracts*, vol. 84, 1976).

*Primary Examiner*—John M. Ford

[57] ABSTRACT

This invention relates to novel N-(heterocyclicaminocarbonyl) indole sulfonamides which are useful as agricultural chemicals and, in particular, as herbicides.

41 Claims, No Drawings

HERBICIDAL INDOLE SULFONAMIDES

BACKGROUND OF THE INVENTION

This invention relates to novel N-(heterocyclicaminocarbonyl)indole sulfonamides which are useful as agricultural chemicals and, in particular, as herbicidal agents.

Canadian Pat. No. 747,920 (issued Dec. 6, 1966, Upjohn) discloses 3-(alkylcarbamoylsulfamoyl)-1-alkylindole-2-carboxylic acids and esters (i) as sedatives, diuretics, antifungal agents and/or sun screens

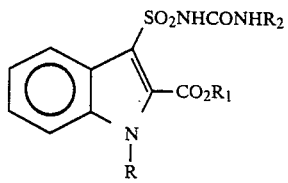

where
R and $R_2$ are $C_1$-$C_4$ alkyl, and
$R_1$ is H or $C_1$-$C_4$ alkyl.

U.S. Pat. No. 4,127,405 teaches compounds which are useful for controlling weeds in wheat having the formula

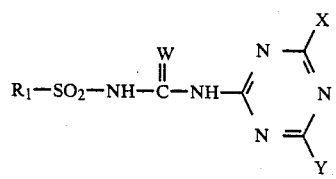

wherein
$R_1$ is

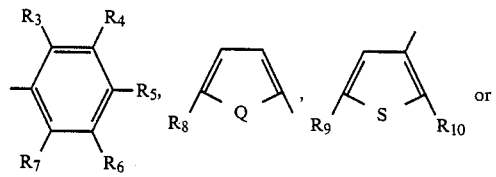

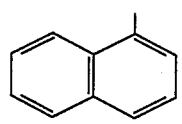

$R_3$ and $R_6$ are independently hydrogen, fluorine, chlorine, bromine, iodine, alkyl of 1-4 carbon atoms, alkoxy of 1-4 carbon atoms, nitro, trifluoromethyl, cyano, $CH_3S(O)_n$— or $CH_3CH_2S(O)_n$—;
$R_4$ is hydrogen, fluorine, chlorine, bromine or methyl;
$R_5$ is hydrogen, fluorine, chlorine, bromine, methyl or methoxy;
$R_7$ is hydrogen, fluorine, chlorine, bromine, alkyl of 1-2 carbon atoms or alkoxy of 1-2 carbon atoms;
$R_a$ is hydrogen, methyl, chlorine or bromine;
$R_9$ and $R_{10}$ are independently hydrogen, methyl, chlorine or bromine;
W and Q are independently oxygen or sulfur;
n is 0, 1 or 2;
X is hydrogen, chlorine, bromine, methyl, ethyl, alkoxy of 1-3 carbon atoms, trifluoromethyl, $CH_3S$— or $CH_3OCH_2$—; and
Y is methyl or methoxy; or their agriculturally suitable salts; provided that:
 (a) when $R_5$ is other than hydrogen, at least one of $R_3$, $R_4$, $R_6$ and $R_7$ is other than hydrogen and at least two of $R_3$, $R_4$, $R_6$ and $R_7$ must be hydrogen;
 (b) when $R_5$ is hydrogen and all of $R_3$, $R_4$, $R_6$ and $R_7$ are other than hydrogen, then all of $R_3$, $R_4$, $R_6$ and $R_7$ must be either chlorine or methyl; and
 (c) when $R_3$ and $R_7$ are both hydrogen, at least one of $R_4$, $R_5$ or $R_6$ must be hydrogen.

French Pat. No. 1,468,747 discloses the following para-substituted phenylsulfonamides, useful as antidiabetic agents:

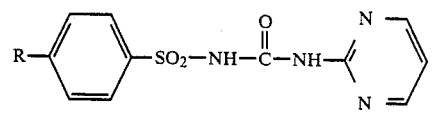

wherein R=H, hydrogen, $CF_3$ or alkyl.

Logemann et al. Chem. Ab., 53, 18052 g (1959), disclose a number of sulfonamides, including uracil derivatives and those having the formula:

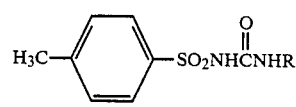

wherein R is butyl, phenyl or

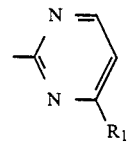

and $R_1$ is hydrogen or methyl. When tested for hypoglycemic effect in rats (oral doses of 25 mg/100 g), the compounds in which R is butyl and phenyl were most potent. The others were of low potency or inactive.

Wojciechowski, J. Acta. Polon. Pharm. 19, p. 121-5 (1962) [Chem Ab., 59 1633 e] describes the syntthesis of N-[(2,6-dimethoxypyrimidin-4-yl)aminocarbonyl]-4-methylbenzenesulfonamide:

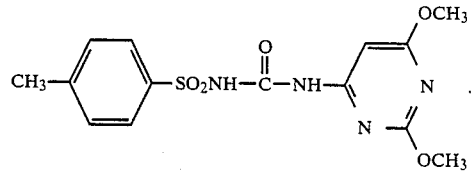

Based upon similarity to a known compound, the author predicted hypoglycemic activity for the foregoing compound.

Netherlands Pat. No. 121,788, published Sept. 15, 1966, teaches the preparation of compounds of Formula (i), and their use as general or selective herbicides,

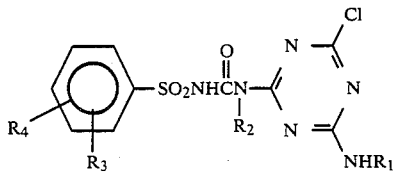

wherein

R₁ and R₂ may independently be alkyl of 1–4 carbon atoms; and

R₃ and R₄ may independently be hydrogen, chlorine or alkyl of 1–4 carbon atoms.

Compounds of Formula (ii), and their use as antidiabetic agents, are reported in *J. Drug. Res.* 123 (1974),

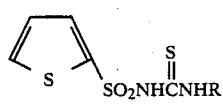

wherein R is pyridyl.

U.S. Patent application Ser. No. 244,172 discloses herbicidal compounds of formulae

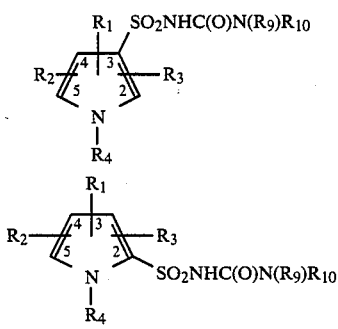

wherein

R₁ is H, C₁–C₄ alkyl, NO₂, CN, C(O)CCl₃, SO₂R₁₁, C(O)R₅ or CO₂H;

R₂ is H or C₁–C₄ alkyl;

R₃ is H, C₁–C₄ alkyl, Cl or Br;

R₄ is H, C₁₁–C₄ alkyl, cyanoethyl, C₅–C₆ cycloalkyl, benzyl, phenyl substituted with Cl or NO₂, or C(O)R₆;

R₅ is C₁–C₄ alkyl or C₁–C₄ alkoxy;

R₆ is C₁–C₄ alkyl, or NR₇R₈;

R₇ and R₈ are independently C₁–C₂ alkyl;

R₉ is H, CH₃ or OCH₃;

R₁₁ is C₁–C₄ alkyl;

R₁₀ is

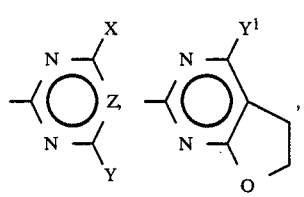

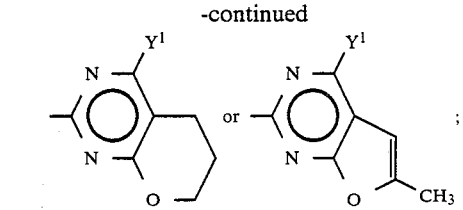

X is CH₃ or OCH₃;

Y is H, CH₃, OCH₃, OCH₂CH₃, OCH₂CF₃, Cl, CH₂OCH₃, CH₂OCH₂CH₃ or CF₃;

Y¹ is H, CH₃, OCH₃, Cl or OCH₂CH₃; and

Z is CH, N, CCH₃ CCH₂CH₃, CCH₂CH₂Cl, CCl, CBr or CF;

and their agriculturally suitable salts.

The presence of undesired vegetation causes substantial damage to useful crops, especially agricultural products that satisfy man's basic food and fiber needs, such as cotton, rice, corn, wheat, and the like. The current population explosion and concomitant world food and fiber shortage demand improvements in the efficiency of producing these crops. Prevention or minimizing the loss of a portion of such valuable crops by killing, or inhibiting the growth of undesired vegetation is one way of improving this efficiency. A wide variety of materials useful for killing, or inhibiting (controlling) the growth of undesired vegetation is available; such materials are commonly referred to as herbicides. The need still exists however, for more effective herbicides.

SUMMARY OF THE INVENTION

This invention relates to novel compounds of Formula I and Formula II, suitable agricultural compositions containing them, and their method of use as general, as well as selective, pre-emergence or post-emergence herbicides.

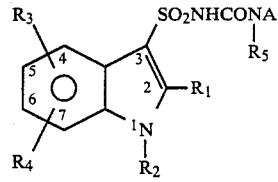

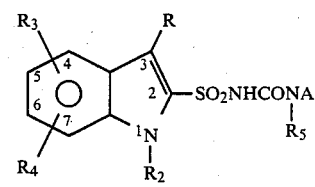

where

R is H, C₁–C₄ alkyl, (CH₂)ₘCO₂R₉, CH₂OC₂H₅, SO₂R₁₀, CHO, SO₂NR₁₁R₁₂, CH₂N(CH₃)₂ or CH₂OCH₃;

R₁ is H, C₁–C₄ alkyl, CO₂R₆, C(O)NR₇R₈, C(O)R₁₀, SO₂R₁₀, or SO₂NR₁₁R₁₂;

R₂ is H, C₁–C₃ alkyl or SO₂C₆H₅;

R₃ is H, F, Cl, Br, C₁–C₃ alkyl, C₁–C₃ alkoxy or NO₂;

R₄ is H, Cl or Br;

R₅ is H or CH₃;

R₆ is C₁–C₄ alkyl, C₃–C₄ alkenyl, CH₂CH₂Cl or CH₂CH₂OCH₃;

R$_7$ and R$_8$ are independently H or C$_1$–C$_4$ alkyl, provided that one total number of carbon atoms is less than or equal to 4;
R$_9$ is H or C$_1$–C$_3$ alkyl;
R$_{10}$ is C$_1$–C$_3$ alkyl;
R$_{11}$ and R$_{12}$ are independently C$_1$–C$_3$ alkyl, provided that the total number of carbon atoms is less than or equal to 4.
m is 0, 1 or 2;
A is

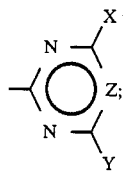

X is CH$_3$ or OCH$_3$;
Y is CH$_3$, OCH$_3$, OC$_2$H$_5$, CH$_2$OCH$_3$, Cl, H, C$_2$H$_5$ or N(CH$_3$)$_2$; and
Z is CH or N;
provided that
(1) when R$_2$ is SO$_2$C$_6$H$_5$, then R$_1$ and R are H or C$_1$14 C$_4$ alkyl.
(2) when Y is Cl, then Z is CH; and
(3) when m is 0, then R$_9$ is C$_1$–C$_3$ alkyl.

PREFERRED COMPOUNDS

Preferred for reasons of higher herbicidal activity and/or more favorable ease of synthesis are:
(1) Compounds of the generic scope of Formula I where R$_1$ is H, C$_1$–C$_3$ alkyl, CO$_2$R$_6$, C(O)NR$_7$R$_8$, SO$_2$NR$_{11}$R$_{12}$ or SO$_2$R$_{10}$; and R$_5$ is H;
(2) Compounds of Preferred (1) where R$_3$ and R$_4$ are H;
(3) Compounds of Preferred (2) where R$_2$ is H or CH$_3$;
(4) Compounds of Preferred (3) where R$_1$ is H, CO$_2$CH$_3$, SO$_2$CH$_3$ or SO$_2$N(CH$_3$)$_2$;
(5) Compounds of Preferred (4) where Y is CH$_3$, OCH$_3$, OC$_2$H$_5$, CH$_2$OCH$_3$ or Cl;
(6) Compounds of the generic scope of Formula II where R is H, C$_1$–C$_3$ alkyl, (CH$_2$)$_m$CO$_2$R$_9$, SO$_2$R$_{10}$ or SO$_2$NR$_{11}$R$_{12}$; and R$_5$ is H;
(7) Compounds of Preferred (6) where R$_3$ and R$_4$ are H;
(8) Compounds of Preferred (7) where R$_2$ is H or CH$_3$;
(9) Compounds of Preferred (8) where R is H, CH$_3$ or (CH$_2$)$_m$CO$_2$—(C$_1$–C$_3$ alkyl); and
(10) Compounds of Preferred (9) where Y is CH$_3$, OCH$_3$, OC$_2$H$_5$, CH$_2$OCH$_3$ or Cl.

Specifically Preferred for highest herbicidal activity and/or most favorable ease of synthesis are:
3-[[(4,6-dimethoxypyrimidin-2-yl)aminocarbonyl-]aminosulfonyl]-1-methyl-1H-indole-2-carboxylic acid, methyl ester;
3-[[(4,6-dimethylpyrimidin-2-yl)aminocarbonyl-]aminosulfonyl]-1-methyl-1H-indole-2-carboxylic acid, methyl ester,
3-[[(4-methoxy-6-methylpyrimidin-2-yl)aminocarbonyl-]aminosulfonyl]-1-methyl-1H-indole-2-carboxylic acid, methyl ester,
3-[[(4,6-dimethoxy-1,3,5-triazin-2-yl)aminocarbonyl-]aminosulfonyl]-1-methyl-1H-indole-2-carboxylic acid, methyl ester,
3-[[(4,6-dimethyl-1,3,5-triazin-2-yl)aminocarbonyl]-aminosulfonyl]1-methyl-1H-indole-2-carboxylic acid, methyl ester;
3-[[(4-methyl-6-methoxy-1,3,5-triazin-2-yl)aminocarbonyl]aminosulfonyl]-1methyl-1H-indole-2-carboxylic acid, methyl ester;
N-[(4,6-dimethoxypyrimidin-2-yl)aminocarbonyl]-3-methyl-1H-indole-2-sulfonamide;
N-[(4,6-dimethylpyrimidin-2-yl)aminocarbonyl]-3-methyl-1H-indole-2-sulfonamide;
N-[(4-methyl-6-methoxypyrimidin-2-yl)aminocarbonyl]-3-methyl-1H-indole-2-sulfonamide;
N-[(4,6-dimethoxy-1,3,5-triazin-2-yl)amniocarbonyl]-3-methyl-1H-indole-2-sulfonamide;
N-[(4,6-dimethoxy-1,3,5-triazin-2-yl)aminocarbonyl]-3-methyl-1H-indole-2-sulfonamide;
N-[(4-methyl-6-methoxy-1,3,5-triazin-2-yl)aminocarbonyl]-3-methyl-1H-indole-2-sulfonamide;
3-[[(4,6-dimethoxypyrimidin-2-yl)aminocarbonyl-]aminosulfonyl]-1H-indole-2-carboxylic acid, ethyl ester,
3-[[(4,6-dimethoxy-1,3,5-triazin-2-yl)aminocarbonyl-]aminosulfonyl]-1H-indole-2-carboxylic acid, ethyl ester,
3-[[(4-methoxy-6-methyl-1,3,5-triazin-2yl)aminocarbonyl]aminosulfonyl]1H-indole-2-carboxylic acid, ethyl ester,
3-[[(4-methoxy-6-methylpyrimidin-2-yl)aminocarbonyl-]aminosulfonyl]-1H-indole-2-carboxylic acid, ethyl ester,
3-[[(4,6-dimethylpyrimidin-2-yl)aminocarbonyl-]aminosulfonyl]-1H-indole-2-carboxylic acid, ethyl ester,

DETAILED DESCRIPTION OF THE INVENTION

A general process for the preparation of compounds of Formula I is illustrated by the following equation:

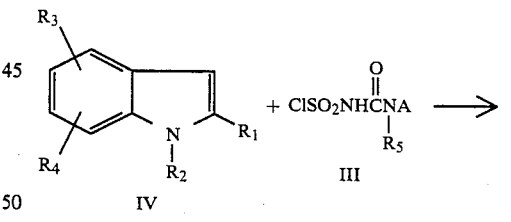

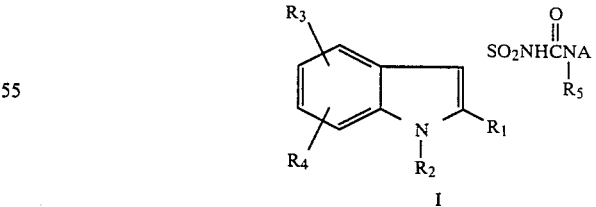

More specifically, the compounds of this invention of Formula I are prepared by contacting a heterocyclilc amine of Formula V and chlorosulfonyl isocyanate to prepare the intermediate of Formula III. These compounds are preferably generated in situ and used without isolation in the synthesis of compounds of Formula I. The aminocarbonyl

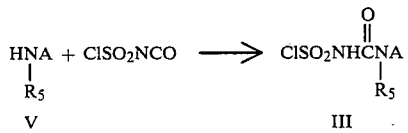

sulfamoyl chloride of Formula III is then contacted with an indole of Formula IV, preferably in the presence of a Friedel-Crafts catlayst, to afford herbicidal indole sulfonamides of Formula I.

The heterocyclic amine of Formula V is dissolved or suspended in an art inert organic solvent, including but not limited to, dichloromethane, nitroethane, nitropropanes, tetrahydrofuran or nitroethane. The reaction mixture is maintained in an inert atmosphere at a temperature of $-80°$ to $0°$ C. When tetrahydrofuran is the solvent, the preferred temperature range is $-80°$ to $-50°$ C.; for nitromethane, the preferred range is $-20°$ to $0°$. One equivalent of chlorosulfonyl isocyanate, either neat or, if tetrahydrofuran is not the solvent, dissolved in the solvent, is contacted with the amine at such a rate as to maintain the reaction temperature within the preferred range. The reaction proceeds rapidly and the reaction mixture is maintained within the preferred temperature range for a period of 0.1 to 1.0 hour to insure complete formation of intermediate III. Compound III is then contacted at a temperature within the preferred range for the solvent employed with an equimolar amount of indole IV, either neat or dissolved in the solvent.

From this point on, the reaction conditions employed depend on the nature of the substituents on the pyrrole ring of the indole nucleus. For reactions with indoles IV in which $R_1$ is H or $C_1$-$C_4$ alkyl and $R_2$ is H or $C_1$-$C_3$ alkyl, a Friedel-Crafts catalyst may optionally be added at a temperature within the preferred range. Friedel-Crafts catlaysts are extensively defined in Volume I, Chapter IV of "Friedel-Crafts and Related Reactions", ed. G. A. Olah, Interscience Publ., New York, 1963. Preferred catalysts are those acidic halides, typified by aluminum chloride and bromide, which posses an electron deficient central metal atom capable of electron acceptance from basic reagents. More preferred is the use of aluminum (III) chloride in a catalytic quantity, the exact amount of which would be apparent to one skilled in the art. The reaction mixture is allowed to warm to ambient temperature and is maintained under an inert atmosphere until completion, usually for a period of from 0.5 to 24 hours. Tetrahydrofuran and nitroethane are the preferred solvents for these reactions.

For reactions with indoles IV in which $R_1$ is other than H or $C_1$-$C_4$ alkyl or in which $R_2$ is $SO_2C_6H_5$, an equimolar amount of a Friedel-Crafts catalyst, preferably aluminum (III) chloride, is added to the reaction mixture at this point. The reaction is allowed to warm to ambient temperature and is then maintained under an inert atmosphere at temperatures ranging from ambient to the boiling point of the solvent employed, with nitromethane being the preferred solvent. The reaction proceeds to completion within 0.5 to 24 hours. In general, higher reaction temperatures and shorter reaction times (0.5 to 4 hours) afford the highest yield. In all cases, the intermediate III is preferably prepared in the same solvent in which the reaction with indole IV is to be carried out.

The compounds of the invention of Formula I may be isolated by partitioning the reaction mixture between dilute aqueous alkali and an organic solvent such as dichloromethane or chloroform. The products are soluble in the aqueous phase and may be precipitated from it after separation of the layers by the addition of a slight excess of an acid such as acetic acid or hydrochloric acid. If the products do not precipitate on acidification they may be isolated by extraction into an organic solvent such as dichloromethane, nitromethane or ethyl acetate followed by evaporation of the solvent. This procedure is most useful in cases in which tetrahydrofuran is the reaction solvent.

When the reaction is carried out in a water-immiscible solvent such as dichloromethane or nitromethane, isolation of the products may best be carried out by contacting the reaction mixture with water, followed by separation of the organic phase and further extraction of the products into an organic solvent such as dichloromethane, nitromethane, nitroethane or ethyl acetate. Evaporation of the organic solution affords the crude products of Formula I.

Purification of the reaction products may be accomplished by trituration with an appropriate solvent, recrystallization or chromatography.

The procedures described generally by Equation 1 are preferred for the preparation of indole sulfonamides of Formula I which $R_1$ is $C_2R_6$, $C(O)R_{10}$, $SO_2R_{10}$ or $SO_2NR_{11}R_{12}$ and $R_2$ is H or $C_1$-$C_3$ alkly or in which $R_1$ is H or $C_1$-$C_4$ alkly and $R_2$ is $C_1$-$C_3$ alkyl or $SO_2C_6H_5$. For cases in which $R_1$ is H, isomeric products of Formulae I and II ($R=R_1=H$) are generally obtained by these methods and may be separated by column chronatography, preparative high pressure or medium pressure chromatography or similar methods.

Indole sulfonamides of Formula I in which $R_1$ is $C(O)NR_7R_8$ are preferably prepared from the corresponding compounds in which $R_1$ is $CO_2CH_3$ by reaction with dialkylaluminum-N-alklamide derivatives as shown in Equation 2. This method is

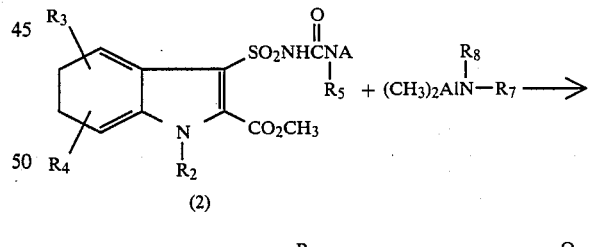

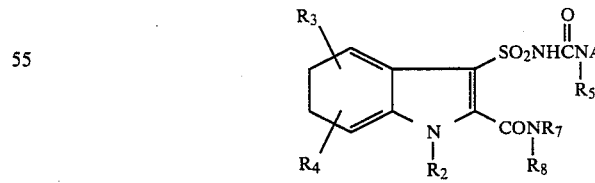

disclosed in unexamined European Pat. No. 7687, filed Feb. 6, 1980.

Indole sulfonamides of Formula I in which $R_1$ is H or $C_1$-$C_4$ alkyl and $R_2$ is H are preferably prepared by alkaline hydrolysis of the corresponding compounds in which $R_2$ is $SO_2C_6H_5$ as shown by equation 3. The reaction is carried out in an excess of aqueous alkali,

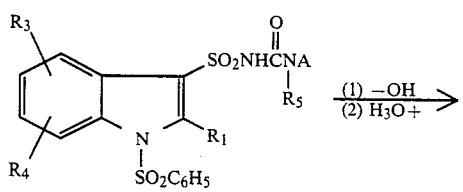

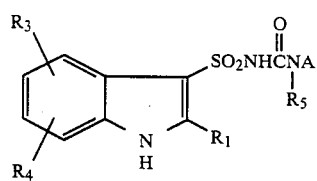

preferably in the presence of a water-miscible co-solvent such as ethanol, dioxane or tetrahydrofuran at temperatures ranging from ambient to the reflux temperature of the solvent mixture employed. After 1 to 24 hours, the reaction mixture is diluted with water and acidified, at 0°–5° with aqueous hydrochloric acid to precipitate the product.

The compounds of this invention of Formula II can be prepared by one of the two methods illustrated below in Equations 4 and 5.

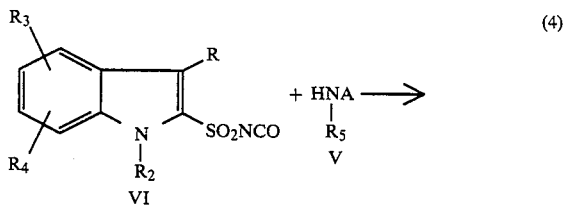

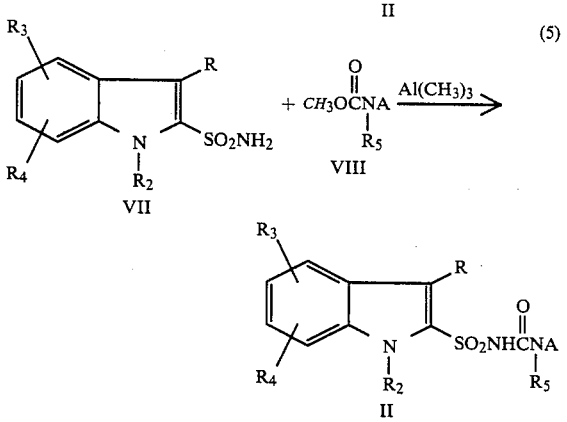

As shown in Equation 4 compounds of Formula II, can be prepared by reacting an amino-hetero-cycle V with an appropriately substituted sulfonyl isocyanate of Formula VI. The reaction is best carried out in inert, aprotic organic solvents such as acetonitrile, methylene chloride or tetrahydrofuran at ambient temperature. The mode of addition is not critical; however, it is often convenient to add a solution of the sulfonyl isocyanate VI to a stirred solution of amino-heterocycle V. The reaction is generally exothermic. In some cases, the desired product is insoluble in the reaction medium and crystallizes from it in pure form. Products soluble in the reaction medium are isolated by evaporated of the solvent, trituration of the residue with solvents such a 1-chlorobutane, methylene chloride or ethyl ether, and filtration.

The intermediate sulfonyl isocyanates of formula VI are prepared by reacting the corresponding sulfonamides of Formula VII with phosgene and n-butyl isocyanate at reflux in a solvent such as xylenes and in the presence of a catalytic amount of a non-nucleophic base such as 1,4-diazabicyclo(2,2,2)octane. Useful procedures are reported by H. Ulrich and A. A. Y. Sayigh, *Newer Methods of Preparative Organic Chemistry*, Vol. VI. pp. 223–241, Academic Press, New York, W. Foerst, Ed.

Compounds of Formula II can also be prepared as shown in Equation 5 by reaction of a sulfonamide of Formula VII with an appropriate methyl carbamate of Formula VIII in the presence of trimethylaluminum. More specifically, the reaction mixture containing sulfonamide VII and an inert, aprotic solvent such as methylene chloride or toluene is reacted under an inert atmosphere with trimethylaluminum and the resulting mixture stirred at ambient temperature until gas evolution ceases. The methyl carbamate VIII is added, generally neat, and the reaction is allowed to proceed at temperatures ranging from ambient to reflux for 16 to 96 hours. The product can be isolated after addition of aqueous hydrochloric acid to the reaction mixture followed by the partitioning of the product into methylene chloride. The product may be purified by crystallization form solvents such as 1-chlorobutane, ethyl ether or methylene chloride or by chromatography.

Either of the methods shown by Equations 4 and 5 is suitable for the preparation of compounds of Formula II in which R is H, $C_1$–$C_4$ alkyl, $SO_2R_{10}$, $SO_2NR_{11}R_{12}$, $CH_2N(CH_3)_2$, $CH_2OCH_2CH_3$ or $CH_2OCH_3$ and $R_2$ is $C_1$–$C_3$ alkyl or $SO_2C_6H_5$. The method of Equation 4 is more preferred for preparation of Compounds II with the above listed values of R where $R_2$ is H. This method is also preferred for preparation of Compounds II in which R is $(CH_2)_mCO_2R_9$, $R_9$ is other than H and $R_2$ is H or $C_1$–$C_3$ alkyl.

Compounds of Formula II in which R is $(CH_2)_mCO_2R_9$, $R_9$ is H and $R_2$ is H or $C_1$–$C_3$ alkyl may best be prepared from the corresponding compounds in which $R_9$ is $C_1$–$C_3$ alkyl by alkaline hydrolysis. Compounds of Formula II in which R is CHO may be prepared from the corresponding compounds in which R is $(CH_2)_mCO_2R_9$, m is 0 and $R_9$ is $CH_3$ (Compound IX) by partial reduction with a reducing agent

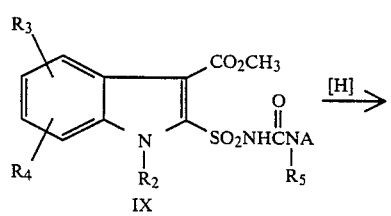

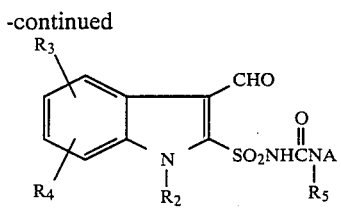

such as diisobutylaluminum hydride. Procedures for these conversions would be apparent to one skilled in the art.

PREPARATION OF REACTANTS

The synthesis of heterocyclic amine derivatives such as those of Formula V has been reviewed in "The Chemistry of Heterocyclic Compounds", a series published by Interscience publ., New York and London. 2-Amino-pyrimidines are described by D. J. Brown in "The Pyrimidines", Vol. XVI of the above series. 2-Amino-1,3,5-triazins are reviewed by E. M. Smolin and L. Rapoport in "s-Triazines and Derivatives," Vol. XIII of the same series. The synthesis of triazines of triazines is also described by F. C. Schaeffer, U.S. 3,154,547 and by K. R. Huffman and F. C. Schaeffer, *J. Org. Chem.*, 28, 1812–1821 (1963).

The heterocyclic amines of Formula V in which $R_5$ is $CH_3$ may be prepared by the following procedure, or by modifications thereof apparent to one skilled in the art.

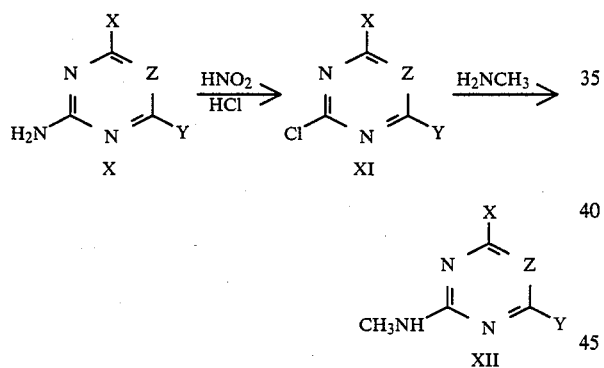

A solution of the amine X in concentrated hydrochloric acid is reacted with an aqueous sodium nitrite solution and the chloro compound XI is isolated in the usual manner by filtration of the acidic solution (see for example, Bee and Rose, *J. Chem. Soc. C.*, 2051 (1966) for the case in which Z is CH and X and Y are $OCH_3$). Displacement of the chlorine may be accomplished by heating with an excess of methylamine in water to obtain the methylaminoheterocycle XII.

Pyrimidinyl and triazinyl methy carbamates of Formula VIII may be prepared by the method illustrated in Equation 6. A heterocyclic amine of Formula V is reacted with one or two equivalents of sodium hydride, when $R_5$ is $CH_3$ or H, respectively,

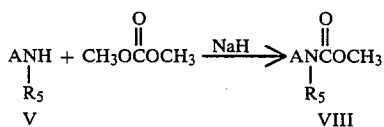

and excess dimethyl carbonate to form VIII.

This reaction takes place in an inert solvent such as tetrahydrofuran at 25° to 70° C. for 1 to 24 hours. The product is isolated by (a) addition of two equivalents of concentrated hydrochloric acid and aqueous saturated sodium chloride and (b) separation of the organic phase followed by concentration to dryness in vacuo.

The preperation of indole derivatives has been extensively reviewed in "Indoles", Parts One-Four, Vol. XXV of the series "The Chemistry of Heterocyclic Compounds" and in "The Chemistry of Indoles", by R. J. Sundberg, Academic Press, New York and London (1970). Two other particularly useful procedures are described by P. G. Gassman in U.S. Pat. No. 3,901,899 and U.S. Pat. No. 3,960,926.

Indoles of Formula IV in which $R_1$ is H, $C_1$-$C_4$ alkyl or $CO_2R_6$ and $R_2$ is H or $C_1$-$C_3$ alkyl are well-known in the literature. Indoles of Formula IV in which $R_1$ is H or $C_1$-$C_4$ alkyl and $R_2$ is $SO_2C_6H_5$ are prepared from the corresponding compounds in which $R_2$ is H by reaction with one equivalent of a base, such as sodium methylsulfonylmethide or n-butyllithium, in ether or tetrahydrofuran, followed by reaction with phenylsulfonyl chloride (see, for example, Sundberg and Russell, *J. Org. Chem.* 38, 3324 (1973) and Saulnier and Gribble, *J. Org. Chem.* 47, 747 (1982)).

Indoles of Formula IV in which $R_1$ is $COR_{10}$, may be prepared via the method of Equation 7. Reaction of N-phenylsulfonyl indoles of Formula XIII in tetrahydrofuran

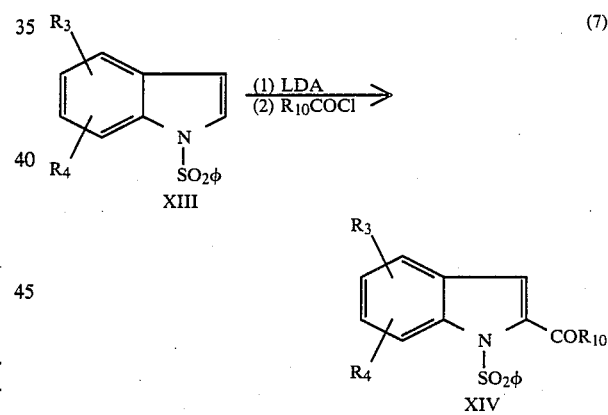

with a slight excess of lithium diisopropylamine (LDA) at low temperature, followed by warming to ambient temperature, recooling and quenching the anion thus formed with an acid chlorid $R_{10}COCl$ results in the formation of compounds of Formula XIV (see, for example, Saulnier and Gribble, ibid.

Indoles of Formula IV in which $R_1$ is $SO_2R_{10}$ may be prepared as illustrated by Equation 8.

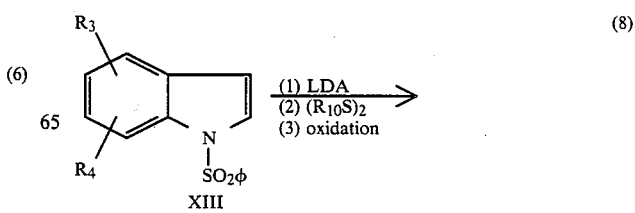

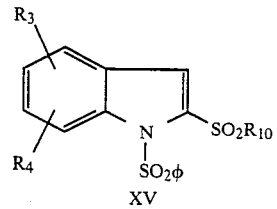

Lithiation of XIII as described above followed by quenching with a dialkyl disulfide $(R_{10}S)_2$ affords N-phenylsulfonyl-2-alkylthioindoles which may be oxidized to alkyl sulfonyl indoles of Formula XV by methods described by Wieland, et. al., *Justus Liebigs Ann. Chem.* 713, 186 (1968) and Hino, et. al., *J. Chem. Soc., Sect. D* 473 (1972).

Equation (9) represents a method of preparation for indoles of Formula IV in which $R_1$ is $SO_2NR_{11}R_{12}$. Lithiation in this method is carried out under an inert atmosphere by the slow addition of an ether solution of XIII to 1.1 equivalents of LDA at 0° followed by stirring at 0° for 0.5 to 2 hours. The resulting slurry is added to a solution of 2 equivalents of sulfonyl chloride in an equal volume of hexanes at −20° to −30°. After 0.5 to 1 hour at −20° to −30°, the reaction mixture is allowed to warm to ambient temperature, stirred until completion (generally 2 to 8 hours), then diluted with water. The N-phenylsulfonyl-2-chlorosulfonyl indoles are isolated by extraction into ethyl acetate and purified by trituration with ether or similar solvents. Reaction of these products with an excess of amine $HNR_{11}R_{12}$ using procedures that would be obvious to one skilled in the art affords indole sulfonamides XVI.

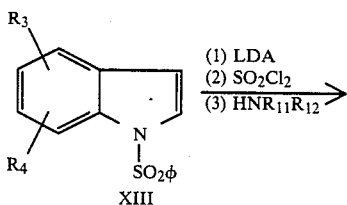

Indoles of Formula IV in which $R_1$ is $COR_{10}$, $SO_2R_{10}$ or $SO_2NR_{11}R_{12}$ and $R_2$ is H are prepared from the corresponding indoles in which $R_2$ is $SO_2C_6H_5$ (compounds XIV, XV and XVI respectively) by alkaline hydrolysis, according to the procedures of Equation 3. In cases in which the product does not precipitate upon acidification, it may be isolated by extraction into ethyl acetate or ether. Alkylation of these indoles on nitrogen by procedures well-known in the literature affords compounds of Formula IV in which $R_1$ is $COR_{10}$, $SO_2R_{10}$ or $SO_2NR_{11}R_{12}$ and $R_2$ is $C_1$-$C_3$ alkyl.

Indole-2-sulfonamides of Formula VII in which R is H, $C_1$-$C_4$ alkyl, $CH_2OCH_3$ or $CH_2OCH_2CH_3$ and $R_2$ is $SO_2C_6H_5$ may be prepared by the method of Equation 10 according to the procedures of Equation 9. The corresponding compounds of Formula VII in which $R_2$ is H may be prepared by alkaline hydrolysis of XVII according

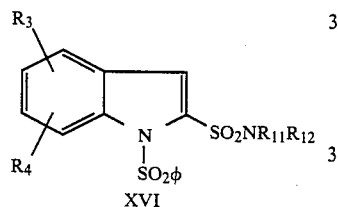

to the procedures of Equation 3. Preparation of the corresponding compounds in which $R_2$ is $C_1$-$C_3$ alkyl may be carried out by the method illustrated below.

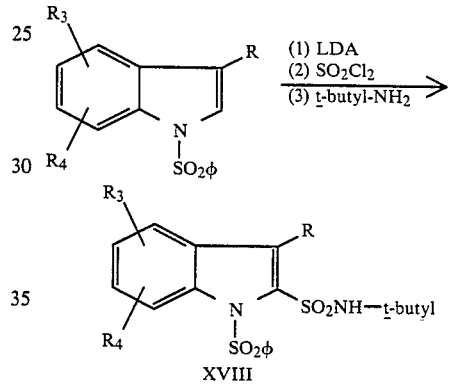

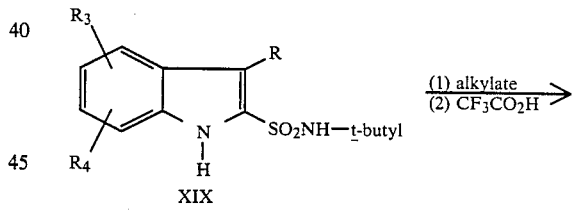

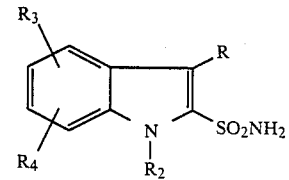

The protected indole-2-sulfonamide of Formula XVIII in which R is H, $C_1$-$C_4$ alkyl, $CH_2OCH_3$ or $CH_2OCH_2CH_3$ is prepared by the method of Equation 9. Alkaline hydrolysis as described above affords XIX which may be alkylated on the more nucleophilic indole nitrogen after dianion formation by procedures which would be known to one skilled in the art. The t-butyl protecting group is then removed with trifluoroacetic acid to afford the desired indole-2-sulfonamides in which $R_2$ is $C_1$-$C_3$ alkyl.

Lithiation of protected indole-2-sulfonamides of Formula XVIII in which R is H (compound XX) provides access to compound of Formula VII in which R is SO$_2$R$_{10}$ or (CH$_2$)$_m$CO$_2$R$_9$ and m is 0 or 1. Reaction of indole XX under an inert atmosphere with 2 equivalents of n-butyl lithium in ether or tetrahydrofuran at −20° to 0°, optionally in the presence of tetraethylenediamine, affords the 3-lithio derivative.

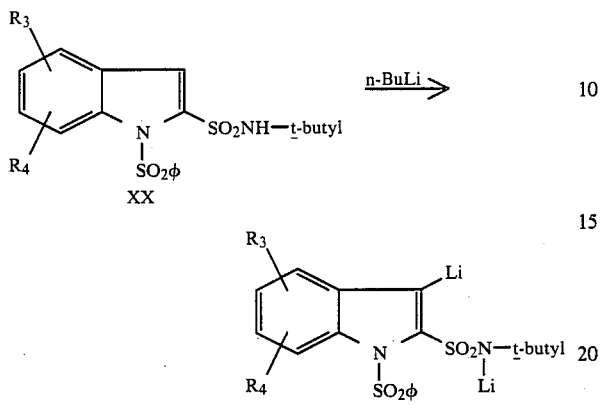

Quenching this anion with A C$_1$–C$_3$ alkyl chloroformate, a C$_1$–C$_3$ alkyl α bromoacetate or a C$_1$–C$_3$ dialkyl disulfide, followed in the last case by oxidation, affords indole-2-sulfonamides of Formula XVIII in which R is (CH$_2$)$_0$CO$_2$R$_9$, (CH$_2$)$_1$CO$_2$R$_9$ or SO$_2$R$_{10}$ respectively. Suitable procedures for these conversions would be known to one skilled in the art. Indole-2-sulfonamides of Formula VII in which R$_2$ is H or C$_1$–C$_3$ alkyl, R is SO$_2$R$_{10}$ or (CH$_2$)$_m$CO$_2$R$_9$ and m is 0 or 1 may then be prepared, using procedures already described or well-known in the literature, by alkaline hydrolysis of the N-phenylsulfonyl group, re-esterification when R is (CH$_2$)$_m$CO$_2$R$_9$, N-alkylation if desired, and removal of the t-butyl protecting group.

Indoles of Formula VII in which R is SO$_2$NR$_{11}$R$_{12}$ are prepared from the corresponding compounds of Formula XXI, obtained by alkaline hydrolysis of XX, by the procedure shown in Equation 12. Reaction of XXI

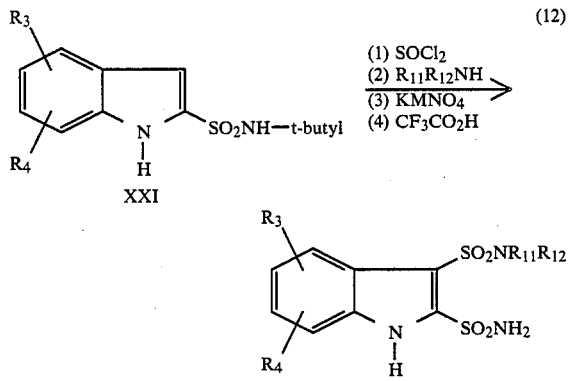

(12)

with thionyl chloride affords the indole-3-sulfonyl chloride, which is converted to the sulfonamide and oxidized to the sulfonamide using procedures described by J. Szmuszkovicz in Canadian Pat. No. 747,920 and in *J. Org. Chem.* 29, 179 (1964). Optional alkylatin of the indole nitrogen followed by trifluoracetic acid hydrolysis as described above afford indoles VII in which R is SO$_2$NR$_{11}$R$_{12}$ and R$_2$ is H or C$_1$–C$_3$ alkyl.

Reaction of indole XXI with acrylic acid in the presence of acetic acid affords the indole-3-propionic acid. Esterification, alkylation of the indole nitrogen, if desired, and trifluoroacetic acid hydrolysis gives rise to indoles of Formula VII in which R is (CH$_2$)$_m$CO$_2$R$_9$, m is 2 and R$_2$ is H or C$_1$–C$_3$ alkyl.

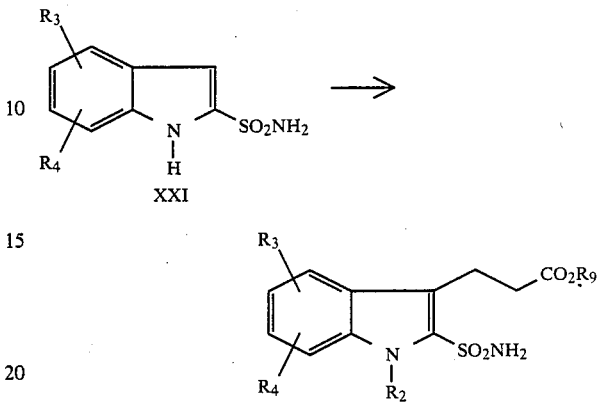

Reaction of indole XXI with formaldehyde and dimethylamine under Mannich reaction conditions followed by optional alkylation of the indole nitrogen and removal of the t-butyl protecting group affords indoles of Formula VII in which R is CH$_2$N(CH$_3$)$_2$ and R$_2$ is H or C$_1$–C$_3$ alkyl.

Agriculturally suitable salts of Formula I and II are also useful herbicides and can be prepared by a number of ways known to the art.

The compounds of the invention and their preparation are further illustrated by the following samples. Unless otherwise indicated, all parts are by weight and all temperatures are in °C.

EXAMPLE 1

Preparation of Methyl 3-[[(4,6-dimethylpyrimidin-2-yl)-aminocarbonyl-]aminosulfonyl]-1-methyl-1H-indole-2-carboxylate.

To a stirred suspension of 2.59 g (0.021 mole) of 2-amino-4,6-dimethylpyrimidine in 75 ml dry nitromethane at −10° was added dropwise under nitrogen via syringe 2.0 ml (0.023 mole) of chlorosulfonyl isocyanate at such a rate as to maintain the temperature below 0°. The resulting clear solution was stirred for 0.5 hour at −5° to −10° and then contacted dropwise with a solution of 3.97 g (0.021 mole) of methyl 1-methyl-1H-indole-2-carboxylate dissolved in 40 ml of dry nitromethane. Upon completion of the addition, 2.95 g (0.022 mole) of aluminum (III) chloride was added in one portion. The reaction mixture was stirred at reflux for 3 hours, then cooled to room temperature and poured into 300 ml H$_2$O. Methylene chloride was added and the layers separated. The aqueous solution was extracted with two additional portions of CH$_2$Cl$_2$ and the combined organic solutions were washed with H$_2$O, dried over MgSO$_4$ and evaporated in vacuo. Trituration of the residue with minimal CH$_2$Cl$_2$ afforded 2.02 g of the desired product as a white solid, m.p. 212°–215° (d). The infrared spectrum of the product included absorptions at 3215 and 3150 (NH), 1730 (C=O), 1710 (C=O), 1345 and 1150 (SO$_2$) cm$^{-1}$, $^1$H NMR (CDCl$_3$/DMSO-d$_6$)δ 2.43 (s, 6H, pyrimidine CH$_3$), 3.88 (s, 6H, ester CH$_3$ and N—CH$_3$), 6.90 (s, 1H, pyrimidine CH), 7.23–7.75 (m, 3H, indole CH), 8.16–8.47 (m, 1H, indole CH), 10.30 (s, 1H, NH), 13.26 (br s, 1H, NH). Mass spectral analysis showed m/e 123,

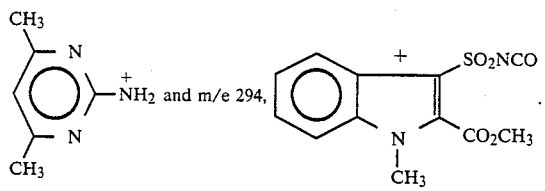

EXAMPLE 2

Preparation of Methyl 3-[[(4-methoxy-6-methyl-pyrimidine-2-yl)aminocarbonyl]aminosulfonyl]-1-methyl-1H-indole-2-carboxylate.

To a stirred suspension of 2.92 g (0.021 mole) of 2-amino-4-methoxy-6-methylpyrimidine in 75 ml dry $CH_3NO_2$ at $-10°$ was added dropwise under nitrogen via syringe 2.0 ml (0.023 mole) of chlorosulfonyl isocyanate at such a rate as to maintain the temperature below 0°. The resulting clear solution was stirred 0.5 hour at $-5°$ to $-10°$ and then contacted dropwise with a solution of 3.97 g (0.021 mole) of methyl 1-methyl-1H-indole-2-carboxylate dissolved in 25 ml of dry nitromethane. Upon completion of the addition, 2.95 g (0.022 mole) of aluminum (III) chloride was added in one portion. The reaction mixture was stirred at reflux for 3 hours, then cooled to room temperature and poured into 300 ml $H_2O$. Dichloromethane was added and the layers were separated. The aqueous solution was extracted with two additional portions of $CH_4Cl_2$ and the combined organic solutions washed with $H_2O$, dried over $MgSO_4$ and evaporated in vacuo. Chromatography on silica gel with 5% acetone in $CH_2Cl_2$ afforded 1.63 g of the desired product as a white solid, m.p. 200°–203° (d). The infrared spectrum of the product included absorptions at 3190 (NH), 1715 (C=O), 1703 (C=O), 1340 and 1150 ($SO_2$) $cm^{-1}$, $^1H$ NMR ($CDCl_3$/DMSO-$d_6$) $\delta 2.45$ (s, 3H, pyrimidine $CH_3$), 3.95 (s, 3H, $OCH_3$), 4.0 (s, 6H, $OCH_3$ N—$CH_3$), 6.37 (s, 1H, pyrimidine CH), 7.23–7.56 (m, 3H, indole CH), 8.18–8.47 (m, 1H, indole CH), 9.50 (s, 1H, NH), 13.08 (br s, 1H, NH). Mass spectral analysis showed m/e 139,

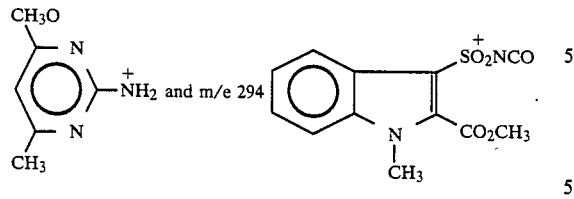

EXAMPLE 3

Preparation of 1-phenylsulfonyl-1H-indole-2-sulfonyl chloride

To a stirred solution of lithium diisopropylamine (prepared from 0.124 mole diisopropylamine in 50 ml ether and 82 ml of 1.6M n-butyllithium in hexanes) at 0° was added dropwise under nitrogen over 40 minutes a solution of 29.2 g (0.1135 mole) of 1-phenylsulfonyl-1H-indole in 400 ml dry ether. The resulting slurry was stirred 30 minutes at 0°, then transferred via canula to a solution of 18.3 ml (0.227 mole) of sulfuryl chloride in 400 ml hexanes at $-20°$ to $-30°$ (dry ice/CCl$_4$ bath). Near the end of the addition there was a gradual 5° exotherm. After 30 min. additional cooling, the ice bath was removed and stirring continued for 4 hours at ambient temperature. The slurry was poured into water and ethyl acetate was added with stirring until all solids dissolved. The layers were separated and the aqueous phase extracted 2 times with ethyl acetate. The combined organic solutions were washed with water, dried over $MgSO_4$ and evaporated in vacuo to a dark semi-solid. Ether trituration afforded 25.07 g of tan solid, m.p. 118°–120° and a second crop of 3.60 g tan solid, m.p. 115°–118°. $^1H$ NMR ($CDCl_3$) $\delta 7.17$–7.84 (m, 7H), 8.03–8.21 (m, 2H), 8.36 (d, 1H, J=9 hz, C-3 proton). The infrared spectrum of the product included absorptions at 1385, 1180 and 1185 $cm^{-1}$ for sulfonyl chloride.

EXAMPLE 4

Preparation of 1-phenylsulfonyl-1H-indole-2-sulfonamide

To a stirred solution of 10 g (0.0281 mole) of 1-phenylsulfonyl-1H-indole-2-sulfonyl chloride in 150 ml anhydrous THF was added at $-78°$ 4 ml (0.192 mole) of anhydrous ammonia. The resulting slurry was allowed to warm to room temperature over 30 minutes, then was sparged with nitrogen to remove excess ammonia. The slurry was filtered and the filtrate evaporated in vacuo to afford 9.19 g of tan solid, m.p. 199°–200.5°, $^1H$ NMR ($CDCl_3$/DMSO-$d_6$) $\delta 7.23$–7.77 (m, 9H), 8.1–8.28 (m, 3H, C-3 proton and $SO_2NH_2$). The infrared spectrum of the product included absorptions at 3400 and 3280 $cm^{-1}$ ($SO_2NH_2$).

EXAMPLE 5

Preparation of 1H-indole-2-sulfonamide

To a stirred solution of 2.4 g (7.13 mmol) of 1-phenylsulfonyl-1H-indole-2-sulfonamide in 50 ml THF was added 0.86 g (21 mmol) of sodium hydroxide dissolved in 5 ml $H_2O$. The mixture was refluxed for 5 hours, then cooled to room temperature, poured into water and acidified slightly with 1N HCl. This solution was extracted 2 times with ethyl acetate and the combined organic layers were dried over $MgSO_4$ and evaporated in vacuo to afford 0.58 g of a pale tan solid, m.p. 190°–192° $^1H$ NMR ($CDCl_3$/DMSO-$d_6$) $\delta 6.92$–7.72 (m, 7H), 11.59 (br, 1H, indole NH). The infrared spectrum of the product included absorptions at 3385, 3280, 1310 and 1140 ($SO_2NH_2$) and at 3340 $cm^{-1}$ (indole NH).

EXAMPLE 6

Preparation of N-[(4.6-dimethylpyrimidin-2-yl) aminocarbonyl]-1H-indole-2-sulfonamide.

A mixture of 5.0 g (0.0255 mole) of 1H-indole-2-sulfonamide, 2.9 ml (0.0255 mole) of n-butylisocyanate, a catalytic amount of 1,4-diazabicyclo[2,2,2] octane and 75 ml of xylenes was heated under nitrogen to 138°. Phosgene was condensed into the reaction mixture until the temperature fell to 130°. As phosgene was consumed, the temperature gradually increased to 138°. Further additions of phosgene were made until the reaction temperature failed to return to 138°. Unreacted phosgene was removed with a nitrogen stream (2N NaOH trap) and heating was continued for 15 minutes. The reaction mixture was cooled to room temperature, filtered under nitrogen and evaporated in vacuo to afford the sulfonylisocyanate intermediate which was used without purification in the second step of the reaction.

A solution of 1.0 g (4.47 mmol) of the above isocyanate in 5 ml dry acetonitrile was added under nitrogen to a mixture of 0.5 g (4.06 mmol) of 2-amino-4.6-dimethylpyrimidine in 5 ml dry acetonitrile and the mixture allowed to stir overnight at ambient temperature. The precipitate was collected by filtration and washed with ether to afford the desired material.

EXAMPLE 7

Preparation of N-[(4.6-dimethylpyrimidin-2-yl) aminocarbonyl]-1-phenysulfonyl-1H-indole-2-sulfonamide To a slurry of 1.0 g (3.0 mmol) 1-phenylsulfonyl-1H-indole-2-sulfonamide in 20 ml methylene chloride was added under nitrogen at ambient temperature 1.65 ml (3.3 mmol) of a 2M trimethylaluminum solution in toluene. The resulting mixture was stirred until gas evolution had ceased, then 0.54 g (3 mmol) of methyl (4.6-dimethylpyrimidin-2-yl) carbamate was added in one portion. The mixture was stirred at reflux overnight, then cooled to room temperature, poured into 50 ml of ice-cold 5% HCl and stirred 5 minutes. The layers were separated and the aqueous phase extracted 2 times with ethyl acetate. The combined organic layers were washed with $H_2O$, dried over $MgSO_4$ and evaporated in vacuo to afford the desired product.

By using methods described generally above and illustrated in Examples 1 through 7, compounds as shown in the following tables can similarly be prepared. These tables are not meant to be all inclusive but only illustrative of the breadth of the invention.

TABLE I

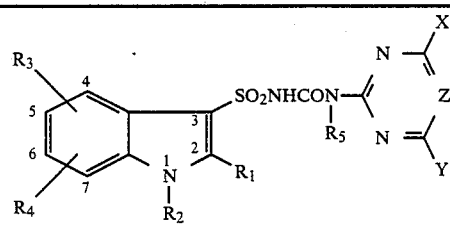

| $R_1$ | $R_2$ | $R_3$ | $R_4$ | $R_5$ | X | Y | Z | m.p. (°C.) |
|---|---|---|---|---|---|---|---|---|
| H | H | H | H | H | $CH_3$ | $CH_3$ | CH | |
| H | H | H | H | H | $CH_3$ | $OCH_3$ | CH | |
| H | $CH_3$ | H | H | H | $CH_3$ | $OCH_3$ | N | |
| H | $C_3H_7$ | H | H | $CH_3$ | $OCH_3$ | $OCH_3$ | CH | |
| H | $C_2H_5$ | 5-$NO_2$ | H | H | $CH_3$ | $CH_2OCH_3$ | N | |
| H | H | H | 6-Cl | H | $OCH_3$ | Cl | CH | |
| H | H | H | H | H | $OCH_3$ | $N(CH_3)_2$ | CH | |
| H | $SO_2C_6H_5$ | H | H | H | $CH_3$ | $CH_3$ | CH | |
| H | $SO_2C_6H_5$ | H | H | H | $OCH_3$ | $CH_3$ | N | |
| H | $SO_2C_6H_5$ | 5-Cl | 7-Cl | H | $CH_3$ | $OCH_2CH_3$ | CH | |
| H | $SO_2C_6H_5$ | 6-$CH_3$ | H | $CH_3$ | $CH_3$ | H | CH | |
| $CH_3$ | H | H | H | H | $OCH_3$ | $CH_3$ | CH | |
| $CH_3$ | H | H | H | H | $OCH_3$ | $CH_3$ | N | |
| $CH_3$ | H | H | H | H | $CH_3$ | $CH_3$ | N | |
| $CH_3$ | H | H | H | H | $CH_3$ | $CH_3$ | CH | |
| $CH_3$ | H | H | H | $CH_3$ | $OCH_3$ | $OCH_3$ | CH | |
| $CH_3$ | $CH_3$ | H | H | H | $OCH_3$ | $CH_3$ | N | |
| $CH_3$ | $CH_3$ | H | H | H | $OCH_3$ | $CH_3$ | CH | |
| $CH_3$ | $CH_3$ | H | H | H | $CH_3$ | $CH_3$ | CH | |
| $CH_3$ | $CH_3$ | H | H | H | $OCH_3$ | $OCH_3$ | CH | |
| $CH_3$ | $C_2H_5$ | 5-Cl | H | H | $CH_3$ | $CH_3$ | N | |
| $C_2H_5$ | H | 6-$OCH_3$ | H | H | $OCH_3$ | $CH_3$ | CH | |
| $C_2H_5$ | $C_2H_5$ | H | H | H | $OCH_3$ | $OCH_3$ | N | |
| $C_2H_5$ | H | H | H | H | $CH_3$ | $CH_2OCH_3$ | CH | |
| n-$C_4H_9$ | H | H | H | H | $CH_3$ | $CH_3$ | N | |
| s-$C_4H_9$ | H | 7-$C_2H_5$ | H | H | $CH_3$ | $OCH_3$ | N | |
| i-$C_3H_7$ | $CH_3$ | H | H | H | $OCH_3$ | $CH_3$ | CH | |
| i-$C_3H_7$ | $CH_3$ | H | H | H | $OCH_3$ | $CH_3$ | N | |
| i-$C_3H_7$ | $CH_3$ | H | H | H | $OCH_3$ | $OCH_3$ | CH | |
| i-$C_3H_7$ | $CH_3$ | H | H | H | $CH_3$ | $CH_3$ | CH | |
| i-$C_3H_7$ | H | H | H | H | $CH_3$ | $CH_3$ | N | |
| i-$C_3H_7$ | H | H | H | $CH_3$ | $OCH_3$ | $CH_3$ | N | |
| i-$C_3H_7$ | H | H | H | H | $OCH_3$ | $CH_3$ | CH | |
| i-$C_3H_7$ | H | 4-$OC_3H_7$ | H | H | $CH_3$ | $CH_3$ | CH | |
| i-$C_3H_7$ | H | H | H | H | $OCH_3$ | $OCH_3$ | CH | |
| i-$C_3H_7$ | $CH_3$ | H | H | H | $CH_3$ | $CH_3$ | N | |
| i-$C_3H_7$ | i-$C_3H_7$ | H | 7-Br | H | $CH_3$ | $CH_2OCH_3$ | N | |
| $CO_2CH_3$ | $CH_3$ | H | H | H | $CH_3$ | $CH_3$ | CH | 212–215(d) |
| $CO_2CH_3$ | $C_2H_5$ | 7-Cl | 5-Cl | H | $CH_3$ | $CH_2OCH_3$ | CH | |
| $CO_2CH_3$ | $C_2H_5$ | H | H | H | $CH_3$ | $CH_3$ | CH | |
| $CO_2CH_3$ | $C_3H_7$ | H | H | H | $OCH_3$ | $CH_3$ | N | |
| $CO_2CH_3$ | $C_3H_7$ | H | H | H | $OCH_3$ | $CH_3$ | N | |
| $CO_2C_2H_5$ | H | H | H | H | $OCH_3$ | $CH_3$ | N | 205–207 |
| $CO_2C_2H_5$ | H | H | H | H | $OCH_3$ | $CH_3$ | CH | 143–145(d) |
| $CO_2C_2H_5$ | H | H | H | H | $CH_3$ | $CH_3$ | N | 134–138(d) |
| $CO_2C_2H_5$ | H | H | H | H | $CH_3$ | $CH_3$ | N | |
| $CO_2C_2H_5$ | H | H | H | H | $OCH_3$ | $OCH_3$ | N | 165–169(d) |
| $CO_2C_2H_5$ | H | H | H | H | $OCH_3$ | $OCH_3$ | CH | 197–201 |
| $CO_2C_2H_5$ | H | H | H | H | $CH_3$ | $N(CH_3)_2$ | CH | |

TABLE I-continued

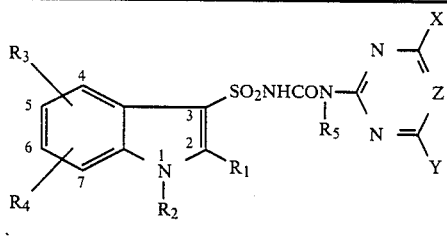

| R₁ | R₂ | R₃ | R₄ | R₅ | X | Y | Z | m.p. (°C.) |
|---|---|---|---|---|---|---|---|---|
| CO₂C₂H₅ | H | 5-OC₂H₅ | H | H | OCH₃ | OCH₃ | N | |
| CO₂C₂H₅ | H | H | H | CH₃ | OCH₃ | OCH₃ | CH | |
| CO₂C₂H₅ | H | 5-C₂H₅ | H | H | CH₃ | CH₃ | CH | 123–217(d) |
| CO₂C₂H₅ | CH₃ | H | 4-Br | H | CH₃ | OCH₃ | N | |
| CO₂C₂H₅ | CH₃ | H | H | H | CH₃ | OCH₃ | CH | |
| CO₂C₂H₅ | CH₃ | H | H | H | CH₃ | CH₂OCH₃ | CH | |
| CO₂-i-Pr | H | 4-F | H | H | OCH₃ | OCH₃ | N | |
| CO₂-i-Pr | H | H | H | H | OCH₃ | OCH₃ | CH | |
| CO₂-i-Pr | H | H | H | H | OCH₃ | CH₃ | CH | |
| CO₂-i-Pr | H | 6-OC₂H₅ | H | H | OCH₃ | CH₃ | N | |
| CO₂-i-Pr | H | H | H | H | CH₃ | CH₃ | CH | |
| CO₂-i-Pr | H | 6-Br | H | H | CH₃ | CH₃ | N | |
| CO₂-i-Pr | CH₃ | H | H | H | CH₃ | OCH₃ | N | |
| CO₂-i-Pr | H | H | H | H | CH₃ | OCH₃ | CH | |
| CO₂-i-Pr | H | H | H | H | CH₃ | CH₃ | CH | |
| CO₂-i-Pr | CH₃ | H | 6-Br | CH₃ | CH₃ | CH₃ | N | |
| CO₂-i-Pr | CH₃ | H | H | H | OCH₃ | OCH₃ | CH | |
| CO₂-i-Pr | CH₃ | H | H | H | OCH₃ | OCH₃ | N | |
| CO₂-i-Pr | C₂H₅ | 5-CH₃ | H | H | OCH₃ | OC₂H₅ | N | |
| CO₂-i-Pr | i-C₃H₇ | 7-C₃H₇ | H | H | OCH₃ | H | N | |
| CO₂-allyl | H | H | H | H | OCH₃ | OCH₃ | N | |
| CO₂-allyl | H | H | H | H | OCH₃ | OCH₃ | CH | |

TABLE I-continued

| R₁ | R₂ | R₃ | R₄ | R₅ | X | Y | Z | m.p. (°C.) |
|---|---|---|---|---|---|---|---|---|
| $CO_2$-allyl | H | H | H | H | $OCH_3$ | $CH_3$ | N | |
| $CO_2$-allyl | H | H | H | H | $OCH_3$ | $CH_3$ | CH | |
| $CO_2$-allyl | H | 5-Br | H | $CH_3$ | $CH_3$ | $CH_2CH_3$ | N | |
| $CO_2$-allyl | H | H | H | H | $CH_3$ | $CH_3$ | CH | |
| $CO_2$-allyl | $CH_3$ | H | H | H | $CH_3$ | $OCH_3$ | N | |
| $CO_2$-allyl | $CH_3$ | H | H | H | $CH_3$ | $OCH_3$ | CH | |
| $CO_2$-allyl | $CH_3$ | H | H | H | $CH_3$ | $CH_3$ | N | |
| $CO_2$-allyl | $CH_3$ | H | H | H | $CH_3$ | $CH_3$ | CH | |
| $CO_2$-allyl | $CH_3$ | H | H | H | $OCH_3$ | $OCH_3$ | CH | |
| $CO_2$-allyl | $CH_3$ | H | H | H | $OCH_3$ | $OCH_2CH_3$ | N | |
| $CO_2$-allyl | $C_3H_7$ | H | H | H | $CH_3$ | $OCH_3$ | N | |
| $CO_2$-allyl | i-$C_3H_7$ | H | H | $CH_3$ | $OCH_3$ | Cl | CH | |
| $CO_2$-allyl | $C_2H_5$ | H | H | H | $OCH_3$ | $CH_3$ | N | |
| $CO_2$-CH(CH₃)CH=CH₂ | H | 4-$OCH_3$ | H | H | $OCH_3$ | $CH_2CH_3$ | CH | |
| $CO_2$-CH₂CH=CH- | H | 6-$NO_2$ | H | H | $CH_3$ | $CH_3$ | CH | |
| $CO_2$-CH₂CH=CH- | $CH_3$ | H | H | H | $CH_3$ | $CH_2OCH_3$ | CH | |
| $CO_2$—t-$C_4H_9$ | H | H | H | H | $CH_3$ | $OCH_3$ | N | |
| $CO_2$n-$C_4H_9$ | H | H | H | H | $OCH_3$ | $OCH_3$ | CH | |
| $CO_2$s-$C_4H_9$ | H | H | H | H | $OCH_3$ | $CH_3$ | CH | |
| $CO_2(CH_2)_2Cl$ | H | H | H | H | $CH_3$ | $CH_3$ | N | |
| $CO_2(CH_2)_2Cl$ | H | 4-$C_2H_5$ | H | H | $OCH_3$ | $CH_3$ | CH | |
| $CO_2(CH_2)_2Cl$ | $CH_3$ | H | H | H | $CH_3$ | $OC_2H_5$ | CH | |
| $CO_2(CH_2)_2Cl$ | H | H | H | $CH_3$ | $CH_3$ | $OCH_3$ | CH | |
| $CO_2(CH_2)_2Cl$ | H | H | H | H | $CH_3$ | $CH_3$ | CH | |
| $CO_2(CH_2)_2OCH_3$ | H | H | H | H | $CH_3$ | Cl | CH | |
| $CO_2(CH_2)_2OCH_3$ | H | H | H | H | $OCH_3$ | $CH_2OCH_3$ | N | |
| $CO_2(CH_2)_2OCH_3$ | H | 7-$OC_3H_7$ | H | H | $OCH_3$ | H | CH | |
| $CO_2(CH_2)_2OCH_3$ | i-$C_3H_7$ | H | H | H | $OCH_3$ | $CH_3$ | CH | |
| $CO_2(CH_2)_2OCH_3$ | H | H | H | H | $OCH_3$ | $CH_3$ | CH | |
| $CO_2(CH_2)_2OCH_3$ | H | H | H | H | $OCH_3$ | $N(CH_3)_2$ | N | |
| $CON(CH_3)_2$ | H | H | 6-Br | H | $OCH_3$ | $OCH_3$ | N | |
| $CON(CH_3)_2$ | H | 7-F | H | H | $CH_3$ | $CH_3$ | N | |

TABLE I-continued

| R₁ | R₂ | R₃ | R₄ | R₅ | X | Y | Z | m.p. (°C.) |
|---|---|---|---|---|---|---|---|---|
| CON(CH₃)₂ | H | H | H | H | CH₃ | CH₃ | CH | |
| CON(CH₃)₂ | H | H | H | H | CH₃ | OCH₃ | CH | |
| CON(CH₃)₂ | H | H | H | H | CH₃ | OCH₃ | N | |
| CON(CH₃)₂ | H | H | H | CH₃ | OCH₃ | OCH₃ | CH | |
| CON(CH₃)₂ | CH₃ | H | H | H | OCH₃ | CH₃ | N | |
| CON(CH₃)₂ | CH₃ | H | H | H | OCH₃ | H | CH | |
| CON(CH₃)₂ | CH₃ | H | H | H | CH₃ | CH₃ | CH | |
| CON(CH₃)₂ | CH₃ | 6-OCH₃ | H | H | OCH₃ | OCH₃ | CH | |
| CON(CH₃)₂ | CH₃ | H | H | H | OCH₃ | OCH₃ | N | |
| CON(CH₃)₂ | CH₃ | H | H | H | CH₃ | CH₃ | N | |
| CON(CH₃)₂ | C₂H₅ | H | H | H | CH₃ | OCH₂CH₃ | N | |
| CON(CH₃)₂ | i-C₃H₇ | H | H | H | CH₃ | OCH₃ | N | |
| CON(CH₃)₂ | C₃H₇ | H | H | H | CH₃ | OCH₃ | CH | |
| CONHCH₃ | H | H | H | H | CH₃ | N(CH₃)₂ | CH | |
| CONHCH₃ | H | H | 7-Cl | CH₃ | OCH₃ | CH₃ | CH | |
| CONHC₂H₅ | H | H | H | H | OCH₃ | CH₃ | N | |
| CONHC₂H₅ | CH₃ | H | H | H | OCH₃ | CH₂OCH₃ | CH | |
| CON(CH₃)C₂H₅ | CH₃ | H | H | H | OCH₃ | OCH₃ | N | |
| CON(CH₃)C₂H₅ | H | 5-F | H | H | OCH₃ | CH₂CH₃ | N | |
| CONHC₃H₇ | H | H | H | H | CH₃ | Cl | CH | |
| CONH—t-C₄H₉ | H | 5-OC₃H₇ | H | H | OCH₃ | CH₃ | N | |
| CON(CH₃)C₃H₇ | H | H | H | H | CH₃ | CH₃ | N | |
| CONH—i-C₄H₉ | H | H | H | CH₃ | OCH₃ | CH₃ | CH | |
| CONH—i-C₃H₇ | H | H | H | H | CH₃ | OCH₃ | N | |
| COCH₃ | H | H | H | H | OCH₃ | OCH₃ | CH | |
| COCH₃ | CH₃ | H | H | H | CH₃ | CH₃ | N | |
| COC₂H₅ | H | H | H | CH₃ | CH₃ | OCH₃ | N | |
| COC₂H₅ | H | H | H | H | CH₃ | CH₃ | CH | |
| COC₂H₅ | H | H | H | H | CH₃ | CH₂OCH₃ | CH | |
| COC₃H₇ | H | 6-NO₂ | H | H | CH₃ | OCH₃ | N | |
| COC₃H₇ | i-C₃H₇ | 4-Br | H | H | OCH₃ | CH₃ | N | |
| COC₃H₇ | H | H | H | H | OCH₃ | CH₃ | N | |
| CO—i-C₃H₇ | H | H | H | H | OCH₃ | CH₃ | CH | |
| CO—i-C₃H₇ | H | H | H | H | OCH₃ | OCH₃ | N | |
| SO₂CH₃ | H | H | H | H | OCH₃ | OCH₃ | N | |
| SO₂CH₃ | H | H | H | H | OCH₃ | OCH₃ | CH | |
| SO₂CH₃ | H | 7-OC₂H₅ | H | CH₃ | CH₃ | OCH₃ | N | |
| SO₂CH₃ | H | H | H | H | CH₃ | OCH₃ | CH | |
| SO₂CH₃ | H | H | H | H | CH₃ | OCH₃ | N | |
| SO₂CH₃ | H | H | H | H | CH₃ | CH₃ | CH | |
| SO₂CH₃ | CH₃ | H | H | H | CH₃ | CH₃ | CH | |
| SO₂CH₃ | CH₃ | H | H | H | CH₃ | CH₃ | N | |
| SO₂CH₃ | CH₃ | 5-OCH₃ | H | H | CH₃ | OCH₃ | N | |
| SO₂CH₃ | CH₃ | H | H | H | CH₃ | OCH₃ | CH | |
| SO₂CH₃ | CH₃ | H | H | H | OCH₃ | OCH₃ | CH | |
| SO₂CH₃ | CH₃ | H | H | H | OCH₃ | OCH₃ | N | |
| SO₂CH₃ | H | H | H | H | CH₃ | C₂H₅ | CH | |
| SO₂CH₃ | H | H | H | H | CH₃ | OC₂H₅ | CH | |
| SO₂CH₃ | H | 4-Cl | 6-Cl | H | CH₃ | Cl | CH | |
| SO₂CH₃ | CH₃ | 4-Cl | H | H | CH₃ | N(CH₃)₂ | CH | |
| SO₂CH₃ | CH₃ | 4-Cl | H | H | OCH₃ | OCH₃ | CH | |
| SO₂CH₃ | CH₃ | 4-Cl | H | H | OCH₃ | Cl | CH | |
| SO₂C₂H₅ | H | H | H | CH₃ | OCH₃ | OCH₃ | N | |
| SO₂C₂H₅ | H | H | 6-Br | H | OCH₃ | OCH₃ | CH | |
| SO₂C₂H₅ | H | H | H | H | OCH₃ | CH₃ | N | |
| SO₂C₂H₅ | H | H | H | H | OCH₃ | CH₃ | CH | |
| SO₂C₂H₅ | H | H | H | H | CH₃ | CH₃ | N | |
| SO₂C₂H₅ | H | 7-Br | H | H | CH₃ | CH₃ | CH | |
| SO₂C₂H₅ | CH₃ | H | H | H | CH₃ | CH₃ | CH | |
| SO₂C₂H₅ | CH₃ | H | H | H | CH₃ | CH₃ | N | |
| SO₂C₂H₅ | CH₃ | H | H | H | CH₃ | OCH₃ | N | |
| SO₂C₂H₅ | CH₃ | H | H | H | CH₃ | OCH₃ | CH | |
| SO₂C₂H₅ | CH₃ | H | H | H | OCH₃ | OCH₃ | N | |
| SO₂C₂H₅ | CH₃ | H | H | H | OCH₃ | OCH₃ | CH | |
| SO₂C₂H₅ | C₃H₇ | H | H | H | OCH₃ | CH₃ | CH | |
| SO₂C₃H₇ | H | H | H | H | OCH₃ | OCH₃ | CH | |
| SO₂C₃H₇ | H | H | H | H | OCH₃ | OCH₃ | N | |
| SO₂C₃H₇ | H | H | H | H | OCH₃ | CH₃ | CH | |
| SO₂C₃H₇ | H | 4-Cl | H | H | OCH₃ | CH₃ | N | |
| SO₂C₃H₇ | H | H | H | H | CH₃ | CH₃ | N | |

TABLE I-continued

| $R_1$ | $R_2$ | $R_3$ | $R_4$ | $R_5$ | X | Y | Z | m.p. (°C.) |
|---|---|---|---|---|---|---|---|---|
| $SO_2C_3H_7$ | H | H | H | H | $CH_3$ | $CH_3$ | CH | |
| $SO_2C_3H_7$ | $CH_3$ | H | H | $CH_3$ | $CH_3$ | $CH_3$ | CH | |
| $SO_2C_3H_7$ | $CH_3$ | H | H | H | $CH_3$ | $CH_3$ | N | |
| $SO_2C_3H_7$ | $CH_3$ | H | H | H | $CH_3$ | $OCH_3$ | CH | |
| $SO_2C_3H_7$ | $CH_3$ | 5-$OCH_3$ | H | H | $CH_3$ | $OCH_3$ | N | |
| $SO_2C_3H_7$ | $CH_3$ | H | H | H | $OCH_3$ | $OCH_3$ | CH | |
| $SO_2C_3H_7$ | $CH_3$ | H | H | H | $OCH_3$ | $OCH_3$ | N | |
| $SO_2C_3H_7$ | $C_2H_5$ | H | H | H | $OCH_3$ | $OCH_3$ | N | |
| $SO_2C_3H_7$ | i-$C_3H_7$ | 4-$NO_2$ | H | H | $CH_3$ | $OCH_3$ | CH | |
| $SO_2N(CH_3)_2$ | H | H | H | H | $CH_3$ | $OCH_3$ | N | |
| $SO_2N(CH_3)_2$ | H | H | H | H | $CH_3$ | $CH_3$ | N | |
| $SO_2N(CH_3)_2$ | H | H | H | $CH_3$ | $CH_3$ | $C_2H_5$ | N | |
| $SO_2N(CH_3)_2$ | H | H | H | H | $CH_3$ | $OCH_3$ | CH | |
| $SO_2N(CH_3)_2$ | H | 5-Cl | 7-Cl | H | $CH_3$ | Cl | CH | |
| $SO_2N(CH_3)_2$ | $CH_3$ | H | H | H | $OCH_3$ | $OC_2H_5$ | CH | |
| $SO_2N(CH_3)_2$ | $C_2H_5$ | H | H | H | $OCH_3$ | $OCH_3$ | CH | |
| $SO_2N(CH_3)_2$ | $C_3H_7$ | H | H | H | $OCH_3$ | $CH_3$ | CH | |
| $SO_2N(CH_3)_2$ | H | H | H | H | $OCH_3$ | $CH_3$ | N | |
| $SO_2N(CH_3)C_2H_5$ | H | H | H | H | $OCH_3$ | $CH_3$ | N | |
| $SO_2N(CH_3)C_2H_5$ | H | H | H | H | $OCH_3$ | $CH_3$ | N | |
| $SO_2N(CH_3)C_2H_5$ | H | 6-Cl | H | H | $OCH_3$ | $N(CH_3)_2$ | N | |
| $SO_2N(CH_3)C_2H_5$ | H | 6-Cl | H | H | $CH_3$ | $OCH_3$ | N | |
| $SO_2N(CH_3)C_2H_5$ | H | 6-Cl | H | $CH_3$ | $CH_3$ | $OCH_3$ | N | |
| $SO_2N(CH_3)C_2H_5$ | H | 6-Cl | H | H | $CH_3$ | $OCH_3$ | CH | |
| $SO_2N(CH_3)C_2H_5$ | $CH_3$ | 5-$C_2H_5$ | H | H | $CH_3$ | $OCH_3$ | CH | |
| $SO_2N(CH_3)C_2H_5$ | $CH_3$ | H | H | H | $CH_3$ | $CH_2OCH_3$ | CH | |
| $SO_2N(CH_3)C_2H_5$ | $CH_3$ | H | H | H | $CH_3$ | $CH_3$ | CH | |
| $SO_2N(CH_3)C_2H_5$ | $C_2H_5$ | H | H | H | $CH_3$ | $CH_3$ | N | |
| $SO_2N(CH_2CH_3)_2$ | H | 5-$NO_2$ | H | $CH_3$ | $OCH_3$ | $CH_3$ | N | |
| $SO_2N(CH_2CH_3)_2$ | H | H | H | H | $OCH_3$ | $OCH_3$ | N | |
| $SO_2N(CH_2CH_3)_2$ | H | H | 6-Br | H | $OCH_3$ | $OCH_3$ | N | |
| $SO_2N(CH_2CH_3)_2$ | $CH_3$ | H | H | H | $OCH_3$ | Cl | CH | |
| $SO_2N(CH_2CH_3)_2$ | $C_2H_5$ | H | H | H | $CH_3$ | $CH_3$ | CH | |
| $SO_2N(CH_3)(CH(CH_3)_2)$ | H | H | H | H | $CH_3$ | $CH_3$ | CH | |
| $SO_2N(CH_3)(CH(CH_3)_2)$ | H | H | H | H | $CH_3$ | H | CH | |
| $SO_2N(CH_3)(CH(CH_3)_2)$ | H | H | H | H | $CH_3$ | $OCH_3$ | N | |
| $SO_2N(CH_3)(CH(CH_3)_2)$ | H | H | H | H | $CH_3$ | $N(CH_3)_2$ | N | |
| $SO_2N(CH_3)(CH(CH_3)_2)$ | i-$C_3H_7$ | H | 5-Br | H | $OCH_3$ | $OCH_3$ | N | |
| $SO_2N(CH_3)(CH(CH_3)_2)$ | H | 7-F | H | H | $OCH_3$ | $OC_2H_5$ | N | |

TABLE I-continued

| $R_1$ | $R_2$ | $R_3$ | $R_4$ | $R_5$ | X | Y | Z | m.p. (°C.) |
|---|---|---|---|---|---|---|---|---|
| $SO_2N\begin{matrix}CH_3\\CH(CH_3)_2\end{matrix}$ | H | H | H | H | $OCH_3$ | $CH_3$ | N | |
| $CH_3$ | $SO_2C_6H_5$ | 6-F | H | $CH_3$ | $CH_3$ | $OCH_3$ | CH | |
| $CH_3$ | $SO_2C_6H_5$ | H | H | H | $OCH_3$ | $CH_3$ | N | |
| $CH_3$ | $SO_2C_6H_5$ | H | H | H | $CH_3$ | $CH_3$ | CH | |
| $C_2H_5$ | $SO_2C_6H_5$ | H | H | H | $CH_3$ | $N(CH_3)_2$ | N | |
| $C_2H_5$ | $SO_2C_6H_5$ | H | H | H | $OCH_3$ | $CH_3$ | N | |
| $i-C_3H_7$ | $SO_2C_6H_5$ | H | H | H | $CH_3$ | $OC_2H_5$ | CH | |
| $CH_3$ | $SO_2C_6H_5$ | 7-$NO_2$ | H | H | $OCH_3$ | $C_2H_5$ | N | |
| $CO_2CH_3$ | H | H | H | H | $CH_3$ | $OCH_3$ | CH | |
| $CO_2CH_3$ | H | H | H | H | $CH_3$ | $CH_3$ | CH | |
| $CO_2CH_3$ | H | H | H | H | $OCH_3$ | $OCH_3$ | CH | |
| $CO_2CH_3$ | H | 5-$OCH_3$ | H | H | $OCH_3$ | $OCH_3$ | N | |
| $CO_2CH_3$ | H | H | H | H | $OCH_3$ | $CH_3$ | N | |
| $CO_2CH_3$ | H | H | H | $CH_3$ | $CH_3$ | $CH_3$ | N | |
| $CO_2CH_3$ | $CH_3$ | H | H | $CH_3$ | $CH_3$ | $CH_3$ | N | |
| $CO_2CH_3$ | $CH_3$ | 6-$C_2H_5$ | H | H | $CH_3$ | $OCH_3$ | N | |
| $CO_2CH_3$ | $CH_3$ | H | H | H | $OCH_3$ | $OCH_3$ | N | |
| $CO_2CH_3$ | $CH_3$ | H | H | H | $OCH_3$ | $OCH_3$ | CH | |
| $CO_2CH_3$ | $CH_3$ | H | H | H | $OCH_3$ | $CH_3$ | CH | 200–203°(d) |
| $CO_2CH_3$ | H | H | H | H | $OCH_3$ | Cl | CH | |
| $CO_2CH_3$ | H | H | H | H | $OCH_3$ | $N(CH_3)_2$ | CH | |
| $CO_2CH_3$ | H | H | H | H | $OCH_3$ | $C_2H_5$ | CH | |
| $CO_2CH_3$ | H | H | H | H | $OCH_3$ | $OC_2H_5$ | N | |

TABLE II

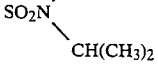

| R | $R_2$ | $R_3$ | $R_4$ | $R_5$ | X | Y | Z | m.p.(°C.) |
|---|---|---|---|---|---|---|---|---|
| H | H | 4-F | H | $CH_3$ | $CH_3$ | $CH_3$ | N | |
| H | H | H | H | H | $CH_3$ | $CH_3$ | CH | |
| H | H | H | H | H | $CH_3$ | $OCH_3$ | N | |
| H | H | H | H | H | $CH_3$ | $OCH_3$ | CH | |
| H | H | H | H | H | $OCH_3$ | $OCH_3$ | CH | |
| H | H | H | H | H | $OCH_3$ | $OCH_3$ | N | |
| H | $CH_3$ | H | H | H | $OCH_3$ | $OCH_3$ | CH | |
| H | $CH_3$ | 5-Cl | H | H | $OCH_3$ | $OCH_3$ | N | |
| H | $CH_3$ | H | H | H | $OCH_3$ | $CH_3$ | N | |
| H | $CH_3$ | H | H | H | $OCH_3$ | $CH_3$ | CH | |
| H | $CH_3$ | H | 4-Br | H | $CH_3$ | $CH_3$ | N | |
| H | $CH_3$ | H | H | H | $CH_3$ | $CH_3$ | CH | |
| H | $C_2H_5$ | H | H | $CH_3$ | $CH_3$ | $CH_3$ | N | |
| H | $i-C_3H_7$ | H | H | H | $CH_3$ | $OC_2H_5$ | CH | |
| H | $SO_2C_6H_5$ | H | H | H | $CH_3$ | $CH_3$ | CH | |
| H | $SO_2C_6H_5$ | H | H | H | $CH_3$ | $OCH_3$ | N | |
| H | $SO_2C_6H_5$ | H | H | H | $CH_3$ | $OCH_3$ | CH | |
| H | $SO_2C_6H_5$ | H | H | H | $OCH_3$ | $OCH_3$ | CH | |
| H | $SO_2C_6H_5$ | H | H | H | $OCH_3$ | $OCH_3$ | CH | |
| H | $SO_2C_6H_5$ | 6-$NO_2$ | H | H | $OCH_3$ | Cl | CH | |
| H | $SO_2C_6H_5$ | H | H | H | $CH_3$ | $N(CH_3)_2$ | CH | |
| $CH_3$ | H | H | 5-Br | H | $OCH_3$ | $OCH_3$ | CH | |
| $CH_3$ | H | H | H | H | $OCH_3$ | $OCH_3$ | N | |
| $CH_3$ | H | 6-$CH_3$ | H | H | $OCH_3$ | $CH_2OCH_3$ | N | |
| $CH_3$ | H | H | H | H | $OCH_3$ | $CH_3$ | N | |
| $CH_3$ | H | H | H | H | $OCH_3$ | $CH_3$ | CH | |

TABLE II-continued

| R | R₂ | R₃ | R₄ | R₅ | X | Y | Z | m.p.(°C.) |
|---|---|---|---|---|---|---|---|---|
| CH₃ | H | H | H | H | CH₃ | CH₃ | N | |
| CH₃ | H | 6-C₃H₇ | H | H | CH₃ | CH₃ | CH | |
| CH₃ | CH₃ | H | H | H | CH₃ | CH₃ | CH | |
| CH₃ | CH₃ | H | H | CH₃ | CH₃ | CH₃ | N | |
| CH₃ | CH₃ | H | H | H | OCH₃ | CH₃ | N | |
| CH₃ | CH₃ | H | H | H | OCH₃ | CH₃ | CH | |
| CH₃ | CH₃ | 5-OC₃H₇ | H | H | OCH₃ | OCH₃ | N | |
| CH₃ | CH₃ | H | H | H | OCH₃ | OCH₃ | CH | |
| CH₃ | C₂H₅ | H | H | CH₃ | OCH₃ | CH₃ | CH | |
| CH₃ | n-C₃H₇ | H | H | H | OCH₃ | CH₃ | N | |
| CH₃ | C₂H₅ | 4-Br | H | H | CH₃ | H | CH | |
| CH₃ | CH₃ | 4-Cl | 6-Cl | H | CH₃ | Cl | CH | |
| CH₃ | SO₂C₆H₅ | H | H | H | CH₃ | OCH₃ | CH | |
| CH₃ | SO₂C₆H₅ | H | H | H | CH₃ | OCH₃ | N | |
| CH₃ | SO₂C₆H₅ | H | H | H | OCH₃ | OCH₃ | CH | |
| CH₃ | SO₂C₆H₅ | H | H | H | OCH₃ | OCH₃ | N | |
| CH₃ | SO₂C₆H₅ | H | H | H | CH₃ | CH₃ | N | |
| CH₃ | SO₂C₆H₅ | H | H | CH₃ | CH₃ | C₂H₅ | N | |
| CH₃ | SO₂C₆H₅ | 5-NO₂ | H | H | CH₃ | OCH₃ | N | |
| C₂H₅ | H | H | H | H | CH₃ | OCH₃ | N | |
| C₂H₅ | H | H | H | H | CH₃ | OCH₃ | CH | |
| C₂H₅ | H | H | H | H | CH₃ | OCH₃ | CH | |
| C₂H₅ | C₂H₅ | 4-OCH₃ | H | H | CH₃ | OC₂H₅ | CH | |
| C₂H₅ | C₂H₅ | H | H | CH₃ | CH₃ | OCH₃ | CH | |
| C₂H₅ | i-C₃H₇ | H | H | H | CH₃ | N(CH₃)₂ | N | |
| C₂H₅ | SO₂C₆H₅ | H | H | H | OCH₃ | OCH₃ | N | |
| C₂H₅ | SO₂C₆H₅ | H | H | H | OCH₃ | OCH₃ | N | |
| C₂H₅ | SO₂C₆H₅ | H | H | H | OCH₃ | CH₃ | N | |
| C₂H₅ | SO₂C₆H₅ | H | 5-Cl | H | OCH₃ | CH₃ | N | |
| n-C₃H₇ | H | H | H | H | OCH₃ | CH₃ | N | |
| n-C₃H₇ | H | H | H | H | OCH₃ | CH₃ | CH | |
| n-C₃H₇ | CH₃ | H | H | H | OCH₃ | CH₂OCH₃ | CH | |
| n-C₃H₇ | C₃H₇ | 6-F | H | H | OCH₃ | OCH₃ | CH | |
| n-C₃H₇ | SO₂C₆H₅ | H | H | CH₃ | OCH₃ | OCH₃ | CH | |
| n-C₃H₇ | SO₂C₆H₅ | H | H | H | CH₃ | N(CH₃)₂ | CH | |
| i-C₃H₇ | H | H | H | CH₃ | OCH₃ | C₂H₅ | N | |
| i-C₃H₇ | H | H | H | H | OCH₃ | CH₃ | CH | |
| i-C₃H₇ | H | H | H | H | OCH₃ | CH₃ | N | |
| i-C₃H₇ | CH₃ | H | H | H | OCH₃ | CH₃ | N | |
| n-C₃H₇ | H | H | H | H | CH₃ | CH₃ | CH | |
| n-C₃H₇ | H | H | H | H | CH₃ | N(CH₃)₂ | CH | |
| n-C₃H₇ | H | 5-Br | 7-Br | H | CH₃ | CH₃ | CH | |
| n-C₃H₇ | i-C₃H₇ | H | H | H | CH₃ | CH₃ | CH | |
| n-C₄H₉ | H | H | H | H | CH₃ | OC₂H₅ | N | |
| n-C₄H₉ | H | H | H | H | OCH₃ | OCH₃ | CH | |
| n-C₄H₉ | C₂H₅ | H | H | H | OCH₃ | OCH₃ | N | |
| s-C₄H₉ | H | H | H | H | OCH₃ | Cl | CH | |
| s-C₄H₉ | H | 6-OC₂H₅ | H | CH₃ | OCH₃ | CH₃ | CH | |
| s-C₄H₉ | H | H | H | H | OCH₃ | CH₃ | CH | |
| t-C₄H₉ | H | H | H | H | OCH₃ | H | CH | |
| t-C₄H₉ | CH₃ | H | 4-Cl | H | OCH₃ | CH₃ | N | |
| t-C₄H₉ | SO₂C₆H₅ | H | H | H | CH₃ | OCH₃ | N | |
| i-C₄H₉ | SO₂C₆H₅ | H | H | H | CH₃ | CH₂OCH₃ | N | |
| n-C₄H₉ | SO₂C₆H₅ | H | H | H | CH₃ | CH₃ | N | |
| s-C₄H₉ | SO₂C₆H₅ | H | H | H | OCH₃ | CH₃ | CH | |
| t-C₄H₉ | SO₂C₆H₅ | H | H | H | OCH₃ | OCH₃ | CH | |
| i-C₄H₉ | SO₂C₆H₅ | H | H | H | OCH₃ | OCH₃ | CH | |
| CH₂CO₂CH₃ | H | H | H | H | OCH₃ | OCH₃ | CH | |
| CH₂CO₂CH₃ | H | H | H | CH₃ | OCH₃ | OCH₃ | N | |
| CH₂CO₂CH₃ | H | H | H | H | OCH₃ | CH₃ | CH | |
| CH₂CO₂CH₃ | H | H | H | H | OCH₃ | CH₃ | N | |
| CH₂CO₂CH₃ | H | H | H | H | CH₃ | CH₃ | N | |
| CH₂CO₂CH₃ | H | 6-OCH₃ | H | H | CH₃ | CH₃ | CH | |
| CH₂CO₂CH₃ | H | H | H | H | CH₃ | CH₃ | CH | |
| CH₂CO₂CH₃ | CH₃ | H | H | H | CH₃ | CH₃ | N | |
| CH₂CO₂CH₃ | CH₃ | H | H | H | CH₃ | CH₃ | CH | |
| CH₂CO₂CH₃ | CH₃ | H | H | H | CH₃ | CH₂OCH₃ | N | |
| CH₂CO₂CH₃ | CH₃ | H | H | H | OCH₃ | OCH₃ | N | |
| CH₂CO₂CH₃ | CH₃ | H | H | H | OCH₃ | OCH₃ | CH | |
| CH₂CO₂CH₃ | CH₃ | H | H | H | OCH₃ | CH₃ | N | |

TABLE II-continued

| R | $R_2$ | $R_3$ | $R_4$ | $R_5$ | X | Y | Z | m.p.(°C.) |
|---|---|---|---|---|---|---|---|---|
| $CH_2CO_2CH_3$ | $CH_3$ | 5-Me | H | H | $OCH_3$ | $CH_3$ | CH | |
| $CH_2CO_2CH_3$ | $C_2H_5$ | H | 7-Cl | $CH_3$ | $OCH_3$ | $OC_2H_5$ | CH | |
| $CH_2CO_2CH_3$ | $C_2H_5$ | H | H | H | $CH_3$ | Cl | CH | |
| $CH_2CO_2CH_3$ | i-$C_3H_7$ | H | H | H | $CH_3$ | $OCH_3$ | CH | |
| $CH_2CO_2CH_3$ | n-$C_3H_7$ | 7-F | H | H | $CH_3$ | $OCH_3$ | N | |
| $CH_2CO_2C_2H_5$ | H | H | H | H | $CH_3$ | $CH_3$ | CH | |
| $CH_2CO_2C_2H_5$ | H | H | H | H | $OCH_3$ | $CH_3$ | CH | |
| $CH_2CO_2C_2H_5$ | H | H | H | H | $OCH_3$ | $CH_3$ | N | |
| $CH_2CO_2C_2H_5$ | $C_2H_5$ | H | 6-Br | $CH_3$ | $OCH_3$ | $CH_3$ | N | |
| $CH_2CO_2C_2H_5$ | $C_2H_5$ | H | H | H | $OCH_3$ | $CH_3$ | N | |
| $CH_2CO_2$i-$C_3H_7$ | H | H | H | H | $OCH_3$ | $CH_3$ | N | |
| $CH_2CO_2$i-$C_3H_7$ | H | H | H | H | $CH_3$ | $C_2H_5$ | CH | |
| $CH_2CO_2$i-$C_3H_7$ | H | 4-$NO_2$ | H | H | $CH_3$ | $N(CH_3)_2$ | CH | |
| $CH_2CO_2$i-$C_3H_7$ | $CH_3$ | H | H | H | $CH_3$ | H | CH | |
| $CH_2CO_2$n-$C_3H_7$ | H | H | H | H | $CH_3$ | $OCH_3$ | CH | |
| $CH_2CO_2$n-$C_3H_7$ | H | H | H | $CH_3$ | $OCH_3$ | $OCH_3$ | N | |
| $CH_2CO_2H$ | H | H | H | $CH_3$ | $OCH_3$ | $OCH_3$ | N | |
| $CH_2CO_2H$ | H | H | H | H | $OCH_3$ | $OCH_3$ | CH | |
| $CH_2CO_2H$ | H | H | H | H | $OCH_3$ | $CH_3$ | CH | |
| $CH_2CO_2H$ | H | 6-$OC_2H_5$ | H | H | $OCH_3$ | $CH_3$ | N | |
| $CH_2CO_2H$ | H | H | H | H | $CH_3$ | $CH_3$ | CH | |
| $CH_2CO_2H$ | H | H | H | H | $OCH_3$ | $CH_3$ | N | |
| $CH_2CO_2H$ | $CH_3$ | H | H | H | $CH_3$ | $OCH_3$ | CH | |
| $CH_2CO_2H$ | $CH_3$ | H | H | H | $OCH_3$ | $OCH_3$ | N | |
| $CH_2CO_2H$ | $CH_3$ | H | H | H | $OCH_3$ | $OCH_3$ | CH | |
| $CH_2CO_2H$ | $C_2H_5$ | 7-$NO_2$ | H | $CH_3$ | $OCH_3$ | $OCH_3$ | CH | |
| $CO_2CH_3$ | H | H | H | H | $OCH_3$ | $CH_3$ | N | |
| $CO_2CH_3$ | H | H | H | H | $OCH_3$ | $CH_3$ | CH | |
| $CO_2CH_3$ | H | H | H | H | $OCH_3$ | $OCH_3$ | CH | |
| $CO_2CH_3$ | H | H | H | H | $OCH_3$ | $OCH_3$ | N | |
| $CO_2CH_3$ | H | H | H | H | $CH_3$ | $CH_3$ | CH | |
| $CO_2CH_3$ | H | 7-Br | 6-Br | H | $CH_3$ | Cl | CH | |
| $CO_2CH_3$ | $CH_3$ | H | H | $CH_3$ | $CH_3$ | $C_2H_5$ | CH | |
| $CO_2CH_3$ | $CH_3$ | H | H | H | $CH_3$ | $OCH_3$ | CH | |
| $CO_2CH_3$ | $C_2H_5$ | H | H | H | $CH_3$ | $OCH_3$ | CH | |
| $CO_2CH_3$ | i-$C_3H_7$ | H | H | H | $OCH_3$ | H | CH | |
| $CO_2C_2H_5$ | H | H | H | H | $OCH_3$ | $OCH_3$ | N | |
| $CO_2C_2H_5$ | H | H | H | H | $OCH_3$ | $OCH_3$ | N | |
| $CO_2C_2H_5$ | H | H | H | H | $OCH_3$ | $OCH_3$ | N | |
| $CO_2C_2H_5$ | H | H | H | $CH_3$ | $OCH_3$ | $OCH_3$ | N | |
| $CO_2C_2H_5$ | H | 4-$C_2H_5$ | H | H | $CH_3$ | $CH_2OCH_3$ | CH | |
| $CO_2C_2H_5$ | $CH_3$ | H | H | H | $CH_3$ | $OCH_3$ | CH | |
| $CO_2C_2H_5$ | $CH_3$ | H | H | H | $CH_3$ | $OCH_3$ | CH | |
| $CO_2C_2H_5$ | n-$C_3H_7$ | H | H | H | $OCH_3$ | $OCH_3$ | CH | |
| $CO_2$i-$C_3H_7$ | H | H | H | H | $OCH_3$ | $C_2H_5$ | N | |
| $CO_2$i-$C_3H_7$ | H | H | H | H | $OCH_3$ | $CH_3$ | N | |
| $CO_2$i-$C_3H_7$ | H | H | 5-Cl | H | $OCH_3$ | $OC_2H_5$ | N | |
| $CO_2$i-$C_3H_7$ | H | 7-$OCH_3$ | H | H | $OCH_3$ | Cl | CH | |
| $CO_2$i-$C_3H_7$ | $CH_3$ | H | H | H | $CH_3$ | H | CH | |
| $CO_2$—n-$C_3H_7$ | H | H | H | $CH_3$ | $CH_3$ | $CH_3$ | CH | |
| $CO_2$—n-$C_3H_7$ | H | H | H | H | $CH_3$ | $CH_3$ | N | |
| $CO_2$—n-$C_3H_7$ | H | H | H | H | $CH_3$ | $N(CH_3)_2$ | N | |
| $CO_2$—n-$C_3H_7$ | H | H | H | H | $CH_3$ | $OCH_3$ | N | |
| $CO_2$—n-$C_3H_7$ | $C_2H_5$ | 6-Cl | H | H | $CH_3$ | $OCH_3$ | N | |
| $CO_2$—n-$C_3H_7$ | n-$C_3H_7$ | H | H | H | $CH_3$ | $OCH_3$ | N | |
| $CO_2H$ | H | H | H | H | $OCH_3$ | $CH_3$ | N | |
| $CO_2H$ | H | H | H | H | $OCH_3$ | $CH_3$ | CH | |
| $CO_2H$ | H | H | H | H | $OCH_3$ | $OCH_3$ | N | |
| $CO_2H$ | H | H | H | H | $OCH_3$ | $OCH_3$ | CH | |
| $CO_2H$ | H | H | H | $CH_3$ | $CH_3$ | Cl | CH | |
| $CO_2H$ | $C_2H_5$ | H | H | H | $CH_3$ | $C_2H_5$ | CH | |
| $CO_2H$ | i-$C_3H_7$ | 6-Cl | H | H | $CH_3$ | $OCH_3$ | CH | |
| $CO_2H$ | n-$C_3H_7$ | H | 5-Br | H | $CH_3$ | H | CH | |
| $(CH_2)_2CO_2CH_3$ | H | H | H | H | $OCH_3$ | $OCH_3$ | N | |
| $(CH_2)_2CO_2CH_3$ | H | H | H | H | $OCH_3$ | $OCH_3$ | CH | |
| $(CH_2)_2CO_2CH_3$ | H | H | H | H | $OCH_3$ | $CH_3$ | CH | |
| $(CH_2)_2CO_2CH_3$ | H | H | H | H | $OCH_3$ | $CH_3$ | N | |
| $(CH_2)_2CO_2CH_3$ | H | H | H | H | $OCH_3$ | $OC_2H_5$ | N | |
| $(CH_2)_2CO_2CH_3$ | H | 7-$NO_2$ | H | H | $CH_3$ | $CH_3$ | CH | |

TABLE II-continued

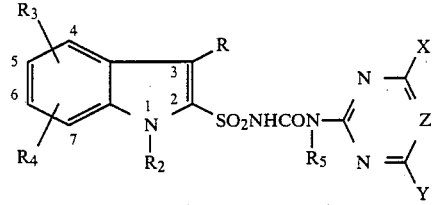

| R | R2 | R3 | R4 | R5 | X | Y | Z | m.p.(°C.) |
|---|---|---|---|---|---|---|---|---|
| (CH$_2$)$_2$CO$_2$CH$_3$ | H | H | 6-Cl | CH$_3$ | CH$_3$ | CH$_3$ | N | |
| (CH$_2$)$_2$CO$_2$CH$_3$ | CH$_3$ | H | H | H | CH$_3$ | CH$_3$ | N | |
| (CH$_2$)$_2$CO$_2$CH$_3$ | CH$_3$ | H | H | H | CH$_3$ | CH$_3$ | N | |
| (CH$_2$)$_2$CO$_2$CH$_3$ | C$_2$H$_5$ | H | H | H | CH$_3$ | CH$_2$OCH$_3$ | N | |
| (CH$_2$)$_2$CO$_2$CH$_3$ | H | H | H | H | OCH$_3$ | Cl | CH | |
| (CH$_2$)$_2$CO$_2$CH$_3$ | H | H | H | H | OCH$_3$ | N(CH$_3$)$_2$ | CH | |
| (CH$_2$)$_2$CO$_2$CH$_3$ | H | H | H | H | OCH$_3$ | OCH$_3$ | CH | |
| (CH$_2$)$_2$CO$_2$CH$_3$ | H | H | H | H | OCH$_3$ | OCH$_3$ | CH | |
| (CH$_2$)$_2$CO$_2$CH$_3$ | H | H | H | CH$_3$ | OCH$_3$ | OCH$_3$ | N | |
| (CH$_2$)$_2$CO$_2$CH$_3$ | C$_2$H$_5$ | 7-Cl | H | H | CH$_3$ | OCH$_3$ | N | |
| (CH$_2$)$_2$CO$_2$CH$_3$ | C$_3$H$_7$ | H | H | H | CH$_3$ | OCH$_3$ | N | |
| (CH$_2$)$_2$CO$_2$i-C$_3$H$_7$ | H | H | H | H | CH$_3$ | C$_2$H$_5$ | N | |
| (CH$_2$)$_2$CO$_2$i-C$_3$H$_7$ | H | H | H | H | CH$_3$ | C$_2$H$_5$ | CH | |
| (CH$_2$)$_2$CO$_2$i-C$_3$H$_7$ | H | H | H | H | OCH$_3$ | CH$_3$ | CH | |
| (CH$_2$)$_2$CO$_2$i-C$_3$H$_7$ | H | H | H | H | OCH$_3$ | CH$_3$ | CH | |
| (CH$_2$)$_2$CO$_2$—n-C$_3$H$_7$ | H | H | H | CH$_3$ | OCH$_3$ | OC$_2$H$_5$ | CH | |
| (CH$_2$)$_2$CO$_2$—n-C$_3$H$_7$ | H | 5-F | H | H | OCH$_3$ | OC$_2$H$_5$ | N | |
| (CH$_2$)$_2$CO$_2$—n-C$_3$H$_7$ | i-C$_3$H$_7$ | H | 6-Br | H | OCH$_3$ | N(CH$_3$)$_2$ | N | |
| (CH$_2$)$_2$CO$_2$—n-C$_3$H$_7$ | CH$_3$ | H | H | H | OCH$_3$ | CH$_3$ | N | |
| (CH$_2$)$_2$CO$_2$H | H | H | H | H | OCH$_3$ | OCH$_3$ | N | |
| (CH$_2$)$_2$CO$_2$H | H | H | H | H | OCH$_3$ | OCH$_3$ | CH | |
| (CH$_2$)$_2$CO$_2$H | H | H | H | H | OCH$_3$ | CH$_3$ | CH | |
| (CH$_2$)$_2$CO$_2$H | H | H | H | H | OCH$_3$ | CH$_3$ | N | |
| (CH$_2$)$_2$CO$_2$H | H | 6-Br | H | H | OCH$_3$ | CH$_3$ | N | |
| (CH$_2$)$_2$CO$_2$H | CH$_3$ | H | H | H | CH$_3$ | CH$_3$ | N | |
| (CH$_2$)$_2$CO$_2$H | n-C$_3$H$_7$ | H | H | CH$_3$ | CH$_3$ | CH$_3$ | N | |
| CH$_2$OC$_2$H$_5$ | H | H | H | H | CH$_3$ | CH$_3$ | CH | |
| CH$_2$OC$_2$H$_5$ | H | H | H | H | CH$_3$ | OCH$_3$ | CH | |
| CH$_2$OC$_2$H$_5$ | H | H | H | H | CH$_3$ | OCH$_3$ | N | |
| CH$_2$OC$_2$H$_5$ | H | H | H | H | OCH$_3$ | OCH$_3$ | N | |
| CH$_2$OC$_2$H$_5$ | H | H | H | H | OCH$_3$ | N(CH$_3$)$_2$ | N | |
| CH$_2$OC$_2$H$_5$ | H | H | 5-Br | H | OCH$_3$ | C$_2$H$_5$ | N | |
| CH$_2$OC$_2$H$_5$ | CH$_3$ | H | H | H | OCH$_3$ | H | N | |
| CH$_2$OC$_2$H$_5$ | CH$_3$ | H | H | H | OCH$_3$ | CH$_2$OCH$_3$ | N | |
| CH$_2$OC$_2$H$_5$ | i-C$_3$H$_7$ | 7-iC$_3$H$_7$ | H | H | CH$_3$ | Cl | CH | |
| CH$_2$OCH$_3$ | H | H | H | CH$_3$ | CH$_3$ | OCH$_3$ | CH | |
| CH$_2$OCH$_3$ | H | H | H | H | CH$_3$ | OCH$_3$ | N | |
| CH$_2$OCH$_3$ | H | H | H | H | CH$_3$ | CH$_3$ | N | |
| CH$_2$OCH$_3$ | H | H | H | H | CH$_3$ | CH$_3$ | CH | |
| CH$_2$OCH$_3$ | H | H | H | H | OCH$_3$ | OCH$_3$ | CH | |
| CH$_2$OCH$_3$ | H | H | H | H | OCH$_3$ | OCH$_3$ | N | |
| CH$_2$OCH$_3$ | H | H | H | H | OCH$_3$ | OCH$_3$ | CH | |
| CH$_2$OCH$_3$ | C$_2$H$_5$ | 4-O—i-C$_3$H$_7$ | H | H | OCH$_3$ | OC$_2$H$_5$ | N | |
| CH$_2$OCH$_3$ | C$_2$H$_5$ | H | H | H | OCH$_3$ | OCH$_3$ | N | |
| CHO | H | H | H | H | CH$_3$ | OCH$_3$ | N | |
| CHO | H | H | H | H | CH$_3$ | OCH$_3$ | CH | |
| CHO | H | H | H | H | CH$_3$ | CH$_3$ | CH | |
| CHO | H | H | H | CH$_3$ | CH$_3$ | OCH$_3$ | CH | |
| CHO | H | H | H | CH$_3$ | CH$_3$ | CH$_2$OCH$_3$ | CH | |
| CHO | CH$_3$ | H | 7-Cl | H | OCH$_3$ | Cl | CH | |
| CHO | CH$_3$ | H | H | H | OCH$_3$ | OCH$_3$ | CH | |
| CHO | CH$_3$ | 5-OCH$_3$ | H | H | OCH$_3$ | N(CH$_3$)$_2$ | CH | |
| SO$_2$CH$_3$ | H | H | H | H | OCH$_3$ | CH$_3$ | N | |
| SO$_2$CH$_3$ | H | H | H | H | OCH$_3$ | CH$_3$ | CH | |
| SO$_2$CH$_3$ | H | H | H | H | OCH$_3$ | OCH$_3$ | CH | |
| SO$_2$CH$_3$ | H | H | H | H | OCH$_3$ | OCH$_3$ | N | |
| SO$_2$CH$_3$ | H | 5-C$_2$H$_5$ | H | H | CH$_3$ | OC$_2$H$_5$ | N | |
| SO$_2$CH$_3$ | H | H | H | CH$_3$ | CH$_3$ | Cl | CH | |
| SO$_2$CH$_3$ | CH$_3$ | H | H | H | CH$_3$ | C$_2$H$_5$ | CH | |
| SO$_2$CH$_3$ | i-C$_3$H$_7$ | H | 7-Br | H | CH$_3$ | H | CH | |
| SO$_2$C$_2$H$_5$ | i-C$_3$H$_7$ | H | H | H | OCH$_3$ | CH$_3$ | CH | |
| SO$_2$C$_2$H$_5$ | i-C$_3$H$_7$ | H | H | H | OCH$_3$ | CH$_3$ | N | |
| SO$_2$C$_2$H$_5$ | i-C$_3$H$_7$ | H | H | H | OCH$_3$ | CH$_3$ | N | |
| SO$_2$C$_2$H$_5$ | C$_2$H$_5$ | H | H | H | OCH$_3$ | CH$_2$OCH$_3$ | N | |
| SO$_2$C$_2$H$_5$ | C$_2$H$_5$ | H | H | H | OCH$_3$ | OCH$_3$ | N | |
| SO$_2$i-C$_3$H$_7$ | H | H | H | CH$_3$ | CH$_3$ | N(CH$_3$)$_2$ | N | |
| SO$_2$i-C$_3$H$_7$ | H | H | H | H | CH$_3$ | OCH$_3$ | N | |
| SO$_2$i-C$_3$H$_7$ | H | H | H | H | CH$_3$ | OCH$_3$ | CH | |
| SO$_2$i-C$_3$H$_7$ | n-C$_3$H$_7$ | 5-OCH$_3$ | H | H | CH$_3$ | OCH$_3$ | CH | |
| SO$_2$—n-C$_3$H$_7$ | H | H | H | H | CH$_3$ | OCH$_3$ | CH | |

TABLE II-continued

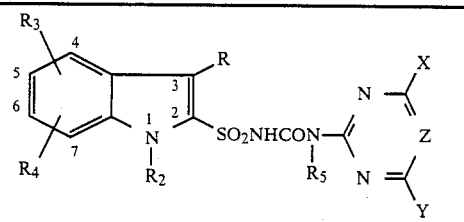

| R | R₂ | R₃ | R₄ | R₅ | X | Y | Z | m.p.(°C.) |
|---|---|---|---|---|---|---|---|---|
| SO₂—n-C₃H₇ | H | H | H | H | CH₃ | C₂H₅ | N | |
| SO₂—n-C₃H₇ | H | H | H | H | OCH₃ | CH₃ | N | |
| SO₂—n-C₃H₇ | CH₃ | H | H | H | OCH₃ | CH₃ | N | |
| SO₂N(CH₃)₂ | H | H | H | H | OCH₃ | CH₃ | N | |
| SO₂N(CH₃)₂ | H | H | H | H | OCH₃ | CH₃ | N | |
| SO₂N(CH₃)₂ | H | H | H | H | OCH₃ | CH₂OCH₃ | CH | |
| SO₂N(CH₃)₂ | H | H | H | H | OCH₃ | OCH₃ | CH | |
| SO₂N(CH₃)₂ | H | H | H | H | CH₃ | OCH₃ | CH | |
| SO₂N(CH₃)₂ | CH₃ | H | H | CH₃ | CH₃ | OCH₃ | CH | |
| SO₂N(CH₃)₂ | CH₃ | H | H | H | CH₃ | OCH₃ | N | |
| SO₂N(CH₃)₂ | i-C₃H₇ | 4-CH₃ | H | H | CH₃ | OCH₃ | N | |
| SO₂N(CH₃)₂ | C₂H₅ | 6-Cl | 4-Cl | H | CH₃ | N(CH₃)₂ | N | |
| SO₂N(CH₃)C₂H₅ | H | H | H | H | OCH₃ | C₂H₅ | N | |
| SO₂N(CH₃)C₂H₅ | H | H | H | H | OCH₃ | OCH₃ | N | |
| SO₂N(CH₃)C₂H₅ | H | H | H | H | CH₃ | OCH₃ | N | |
| SO₂N(CH₃)C₂H₅ | H | H | H | H | CH₃ | OCH₃ | N | |
| SO₂N(CH₃)C₂H₅ | H | H | H | H | CH₃ | OCH₃ | CH | |
| SO₂N(CH₃)C₂H₅ | C₂H₅ | 7-OiC₃H₇ | H | H | CH₃ | OCH₃ | CH | |
| SO₂N(CH₃)C₂H₅ | n-C₃H₇ | H | H | H | CH₃ | N(CH₃)₂ | CH | |
| SO₂N(C₂H₅)₂ | H | H | H | H | OCH₃ | CH₃ | CH | |
| SO₂N(C₂H₅)₂ | H | H | H | CH₃ | OCH₃ | CH₃ | CH | |
| SO₂N(C₂H₅)₂ | H | H | H | H | OCH₃ | CH₃ | N | |
| SO₂N(C₂H₅)₂ | H | H | H | H | OCH₃ | H | N | |
| SO₂N(C₂H₅)₂ | C₂H₅ | H | H | H | OCH₃ | C₂H₅ | N | |
| SO₂N(C₂H₅)₂ | CH₃ | H | 5-Br | H | CH₃ | OC₂H₅ | N | |
| SO₂N(C₂H₅)₂ | CH₃ | 4-CH₃ | H | H | CH₃ | OCH₃ | N | |
| SO₂N(CH₃)C₃H₇ | H | H | H | H | CH₃ | CH₂OCH₃ | N | |
| SO₂N(CH₃)C₃H₇ | H | H | H | H | CH₃ | OCH₃ | N | |
| SO₂N(CH₃)C₃H₇ | H | H | H | CH₃ | OCH₃ | OCH₃ | N | |
| SO₂N(CH₃)C₃H₇ | H | H | H | H | OCH₃ | CH₃ | CH | |
| SO₂N(CH₃)C₃H₇ | n-C₃H₇ | H | H | H | OCH₃ | Cl | CH | |
| SO₂N(CH₃)i-C₃H₇ | n-C₃H₇ | H | H | H | OCH₃ | CH₃ | CH | |
| SO₂N(CH₃)i-C₃H₇ | n-C₃H₇ | H | 7-Cl | H | CH₃ | CH₃ | CH | |
| SO₂N(CH₃)i-C₃H₇ | n-C₃H₇ | H | H | H | CH₃ | OCH₃ | N | |
| SO₂N(CH₃)i-C₃H₇ | C₂H₅ | 5-NO₂ | H | H | CH₃ | OCH₃ | N | |
| CH₂N(CH₃)₂ | H | H | H | H | CH₃ | OCH₃ | N | |
| CH₂N(CH₃)₂ | H | H | H | H | CH₃ | OCH₃ | CH | |
| CH₂N(CH₃)₂ | H | H | H | H | OCH₃ | OCH₃ | CH | |
| CH₂N(CH₃)₂ | H | H | H | H | OCH₃ | OCH₃ | N | |
| CH₂N(CH₃)₂ | H | H | H | H | OCH₃ | N(CH₃)₂ | N | |
| CH₂N(CH₃)₂ | H | H | H | H | CH₃ | OCH₃ | N | |
| CH₂N(CH₃)₂ | CH₃ | H | H | CH₃ | OCH₃ | CH₃ | N | |
| CH₂N(CH₃)₂ | C₂H₅ | H | H | H | OCH₃ | Cl | CH | |
| CH₂N(CH₃)₂ | i-C₃H₇ | H | H | H | OCH₃ | OC₂H₅ | CH | |

FORMULATIONS

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient (s) and at least one of (a) about 0.1% to 20% surfactant (s) and (b) about 1% to 99.9% solid or liquid diluent (s). More specifically, they will contain these ingredients in the following approximate proportions:

TABLE 3

| | Active Ingredient | Weight Percent* Diluent(s) | Surfactant(s) |
|---|---|---|---|
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 5th Ed., McGraw-Hill, New York, 1973, pp. 8–57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley & Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE 8

| Wettable Powder | |
|---|---|
| 3-[[(4-methoxy-6-methylpyrimidin-2-yl)aminocarbonyl]-aminosulfonyl]-1-methyl-1H—indole-2-carboxylic acid, methyl ester | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 9

| Wettable Powder | |
|---|---|
| 3-[[(4,6-dimethyl-1,3,5-triazin-2-yl)-aminocarbonyl]-aminosulfonyl]-1-methyl-1H—indole-2-carboxylic acid, methyl ester | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 10

| Granule | |
|---|---|
| Wettable Powder of Example 9 | 5% |
| attapulgite granules (U.S.S. 20–40 mesh; 0.84–0.42 mm) | 95% |

A slurry of wettable powder containing 25% solids is sprayed on the surface of attapulgite granules in a double-cone blender. The granules are dried and packaged.

EXAMPLE 11

| Extruded Pellet | |
|---|---|
| 3-[[(4,6-dimethoxy-1,3,5-triazin-2-yl)-aminocarbonyl]aminosulfonyl]-1-methyl-1H—indole-2-carboxylic acid, methyl ester | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 12

| Oil Suspension | |
|---|---|
| 3-[[(4,6-dimethoxypyrimidin-2-yl)aminocarbonyl]-aminosulfonyl]-1-methyl-1H—indole-2-carboxylic acid, methyl ester | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 13

| Wettable Powder | |
|---|---|
| N—[(4,6-dimethoxypyrimidin-2-yl)- | 20% |

| Wettable Powder | |
|---|---|
| aminocarbonyl]-3-methyl-1H—indole-2-sulfonamide | |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 14

| Low Strength Granule | |
|---|---|
| N—[(4-methyl-6-methoxypyrimidin-2-yl)aminocarbonyl]-3-methyl-1H—indole-2-sulfonamide | 1% |
| N,N—dimethylformamide | 9% |
| attapulgite granules (U.S.S. 20–40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 15

| Aqueous Suspension | |
|---|---|
| N—[(4,6-dimethylpyrimidin-2-yl)-aminocarbonyl]-3-methyl-1H—indole-2-sulfonamide | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 16

| Solution | |
|---|---|
| N—[(4-methyl-6-methoxy-1,3,5-triazin-2-yl)aminocarbonyl]-3-methyl-1H—indole-2-sulfonamide, sodium salt | 5% |
| water | 95% |

The salt is added directly to the water with stirring to produce the solution, which may then be packaged for use.

EXAMPLE 17

| Low Strength Granule | |
|---|---|
| N—[(4,6-dimethoxy-1,3,5-triazin-2-yl)-aminocarbonyl]-3-methyl-1H—indole-2-sulfonamide | 0.1% |
| attapulgite granules | 99.9% |
| (U.S.S. 20–40 mesh) | |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 18

| Granule | |
|---|---|
| 3-[[(4-methoxy-6-methylpyrimidin-2-yl)aminocarbonyl]aminosulfonyl]-1-methyl-1H—indole-2-carboxylic acid, methyl ester | 80% |
| wetting agent | 1% |
| crude ligninsulfonate salt (containing 5–20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14–100 mesh (1410–149 microns), and packaged for use.

EXAMPLE 19

| High Strength Concentrate | |
|---|---|
| 3-[[(4,6-dimethylpyrimidin-2-yl)aminocarbonyl]aminosulfonyl]-1-methyl-1H—indole-2-carboxylic acid, methyl ester | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE 20

| Wettable Powder | |
|---|---|
| 3-[[(4,6-dimethylpyrimidin-2-yl)aminocarbonyl]aminosulfonyl]-1-methyl-1H—indole-2-carboxylic acid, methyl ester | 90% |
| dioctyl sodium sulfosuccinate | 0.1% |
| synthetic fine silica | 9.9% |

The ingredients are blended and ground in a hammer-mill to produce particles essentially all below 100 microns. The material is sifted through a U.S.S. No. 50 screen and then packaged.

EXAMPLE 21

| Wettable Powder | |
| --- | --- |
| 3-[[(4-methyl-6-methoxy-1,3,5-triazin-2-yl)-aminocarbonyl]-aminosulfonyl]-1-methyl-1H—indole-2-carboxylic acid, methyl ester | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 22

| Oil Suspension | |
| --- | --- |
| N—[(4,6-dimethoxy-1,3,5-triazin-2-yl-aminocarbonyl]-3-methyl-1H—indole-2-sulfonamide | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

UTILITY

The compounds of the present invention are active herbicides. They have utility for broad-spectrum pre- and/or post-emergence weed control in areas where complete control of all vegetation is desired, such as around fuel storage tanks, ammunition depots, industrial storage areas, parking lots, drive-in theaters, around billboards, highway and railroad structures. Alternatively, the subject compounds are useful for the selective weed control in crops, such as wheat, cotton and soybeans.

The rates of application for the compounds of the invention are determined by a number of factors, including their use as selective or general herbicides, the crop species involved, the types of weeds to be controlled, weather and climate, formulations selected, mode of application, amount of foliage present, etc. In general terms, the subject compounds should be applied at levels of around 0.03 to 10 kg/ha, the lower rates being suggested for use on lighter soils and/or those having a low organic matter content, for selective weed control or for situations where only short-term persistence is required.

The compounds of the invention may be used in combination with any other commercial herbicide examples of which are those of the triazine, triazole, uracil, urea, amide, diphenylether, carbamate and bipyridylium types.

The activity of these compounds was discovered in greenhouse tests. The tests are described and the data resulting from them are shown below.

TEST A

Seeds of crabgrass (Digitaria spp.), barnyardgrass (Echinochloa crusgalli), wild oats (Avena fatua), cassia (Cassia tora), morningglory (Ipomoea sp.), cocklebur (Xanthium sp.), sorghum, corn, soybean, rice, wheat and nutsedge tubers (Cyperus rotundus) were planted in a growth medium and treated pre-emergence with the chemicals dissolved in a non phytotoxic solvent solution of the compounds of Table A. At the same time, cotton having five leaves (including cotyledonary ones), bush beans with the third trifoliate leaf expanding, crabgrass, barnyardgrass and wild oats with two leaves, cassia with three leaves (including cotyledonary ones), morningglory and cocklebur with four leaves (including the cotyledonary ones), sorghum and corn with four leaves, soybean with two cotyledonary leaves, rice with three leaves, wheat with one leaf, and nutsedge with three to five leaves were sprayed with a non-phytotoxic solvent solution of the compounds of Table A. Treated plants and controls were maintained in a greenhouse for sixteen days, whereupon all species were compared to controls and visually rated for response to treatment. The ratings for the compounds tested by this procedure are presented in Table A. It will be seen the compounds tested possess high herbicidal activity and that certain compounds are useful for weed control in wheat and soybeans. The ratings are based on a numerical scale extending from 0=no injury, to 10=complete kill. The accompanying descriptive symbols have the following meanings:
 G=growth retardation;
 C=chlorosis/necrosis;
 6Y=abscised buds or flowers;
 U=unusual pigmentation;
 E=emergence inhibition; and
 H=formative effects
 U=unusual pigmentation
 P=terminal bud injury.

TABLE A
POST-EMERGENCE
| | kg/ha | BUSH-BEAN | COTTON | SORGHUM | CORN | SOYBEAN | WHEAT | WILD OATS | RICE | BARNYARD GRASS | CRAB GRASS | MORNING GLORY | COCKLEBUR | CASSIA | NUTSEDGE |
|---|---|---|---|---|---|---|---|---|---|---|---|---|---|---|---|
|  | 0.4 | 6C, 9G, 6Y | 6C, 9G | 9C | 9C | 9C | 5C, 9H | 5C, 9H | 2C, 9G | 9C | 2C, 9G | 2C, 4G | 10C | 6C, 9G | 1C, 8G |
| 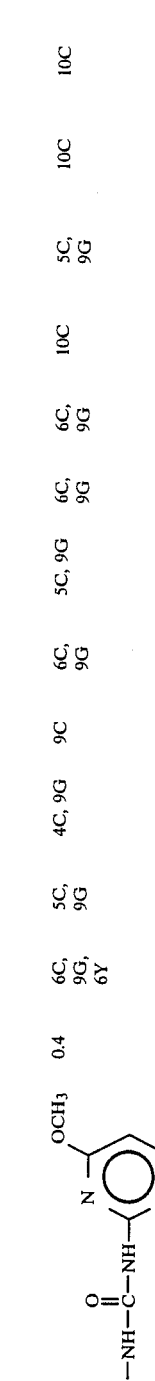 | 0.4 | 6C, 9G, 6Y | 5C, 9G | 4C, 9G | 9C | 6C, 9G | 5C, 9G | 6C, 9G | 6C, 9G | 10C | 5C, 9G | 10C | 10C | 9C | 4C, 8G |
| 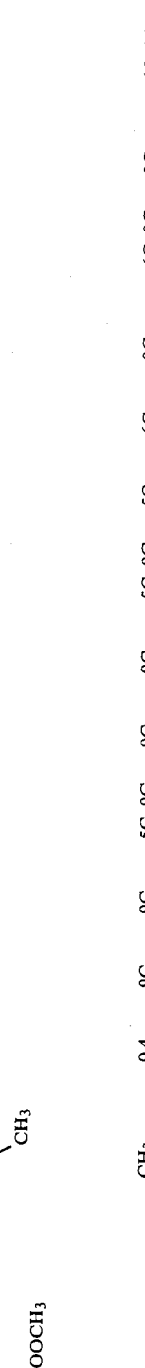 | 0.4 | 9C | 9C | 5C, 9G | 9C | 9C | 5C, 9G | 5C, 9G | 6C, 9G | 9C | 6C, 9G | 9C | 6C, 9G | 6C, 9G | 4C, 9G |
|  | 0.4 | 7C, 9G, 6Y | 6C, 9H | 5C, 9G | 3C, 9G | 9C | 2C, 9G | 2C, 9G | 6C, 9G | 5C, 9H | 5C, 9G | 6C, 9G | 6C, 9G | 9C | 4C, 9G |

TABLE A-continued
| Structure | | | | | | | | | | | | | | | | |
|---|---|---|---|---|---|---|---|---|---|---|---|---|---|---|---|---|
| 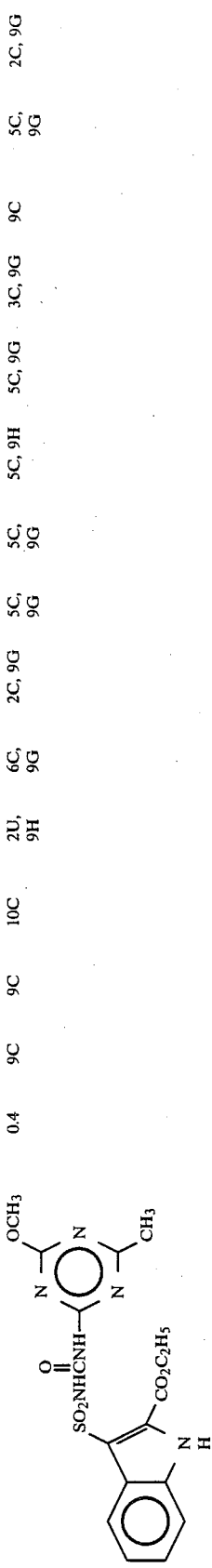 | 0.4 | 9C | 9C | 10C | 2U, 9H | 6C, 9G | 2C, 9G | 5C, 9G | 5C, 9G | 5C, 9H | 5C, 9G | 3C, 9G | 9C | 5C, 9G | 2C, 9G |
| 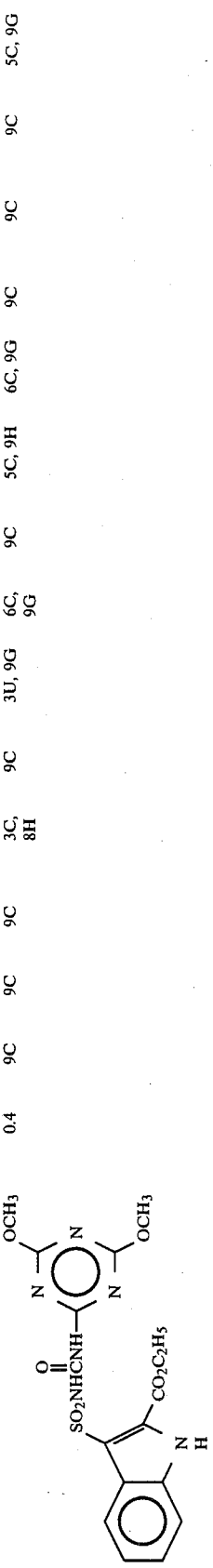 | 0.4 | 9C | 9C | 9C | 3C, 8H | 9C | 3U, 9G | 6C, 9G | 9C | 5C, 9H | 6C, 9G | 9C | 9C | 9C | 5C, 9G |
| 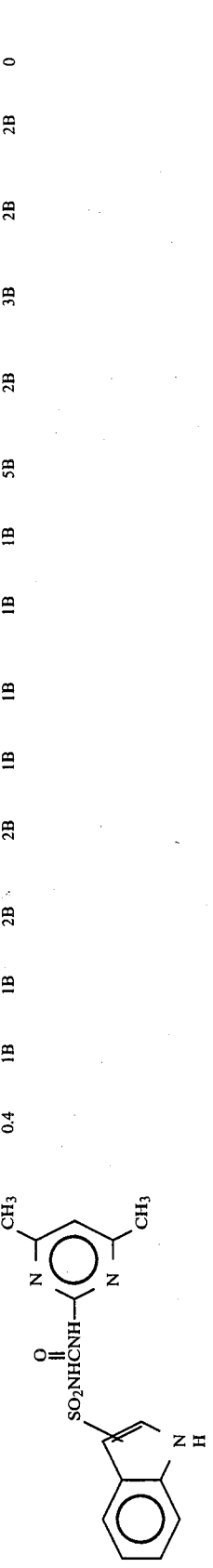 | 0.4 | 1B | 1B | 2B | 2B | 1B | 1B | 1B | 1B | 5B | 2B | 3B | 2B | 2B | 0 |
| 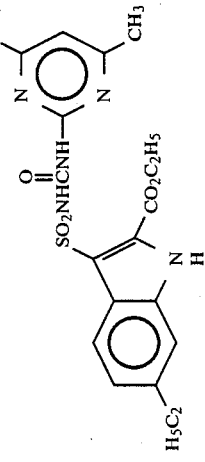 | 0.05 | 2C, 2H | 0 | 0 | 3G | 1H, 5G | 0 | 0 | 1C, 5G | 0 | 0 | 1C | 1C | 1C | 0 |

TABLE A-continued

| Structure | kg/ha | Sorghum | Corn | Soybean | Wheat | Wild Oats | Rice | Barnyard-grass | Crabgrass | Morning-glory | Cocklebur | Cassia | Nutsedge |
|---|---|---|---|---|---|---|---|---|---|---|---|---|---|
| (pyrimidine-SO₂NHCNH, CO₂C₂H₅, indole-NH) | 0.05 | 4C, 8G, 6Y | 2C, 5G | 4C, 9G | 2C, 5G | 2C, 9H | 3C, 8G | 3C, 9H | 5C, 9G | 2C, 9H | 2C, 7G | 3C, 8H | 2C, 6G | 2C, 8G | 3C | 9G |
| (pyrimidine-SO₂NHCNH, indole-N-CH₃) | 0.4 | 2C, 3G | 0 | 0 | 0 | 0 | 0 | 0 | 0 | 0 | 0 | 0 | 0 | 0 | 0 | 0 |

PRE-EMERGENCE

| Structure | kg/ha | Sorghum | Corn | Soybean | Wheat | Wild Oats | Rice | Barnyard-grass | Crabgrass | Morning-glory | Cocklebur | Cassia | Nutsedge |
|---|---|---|---|---|---|---|---|---|---|---|---|---|---|
| (dimethylpyrimidine-SO₂NHCNH-indole-COOCH₃, N-CH₃) | 0.4 | 5C, 9H | 9G | 9H | 9H | 5C | 10E | 5C | 5C | 8G | 9H | 8H | 10E |
| (methoxy-methylpyrimidine-SO₂NHCNH-indole-COOCH₃, N-CH₃) | 0.4 | — | — | 4C, 9G | — | 10E | 6C, 9H | 6C, 9G | 9G | 9H | 8G | 10E |

TABLE A-continued
| Structure | | | | | | | | | | | | | | |
|---|---|---|---|---|---|---|---|---|---|---|---|---|---|---|
| 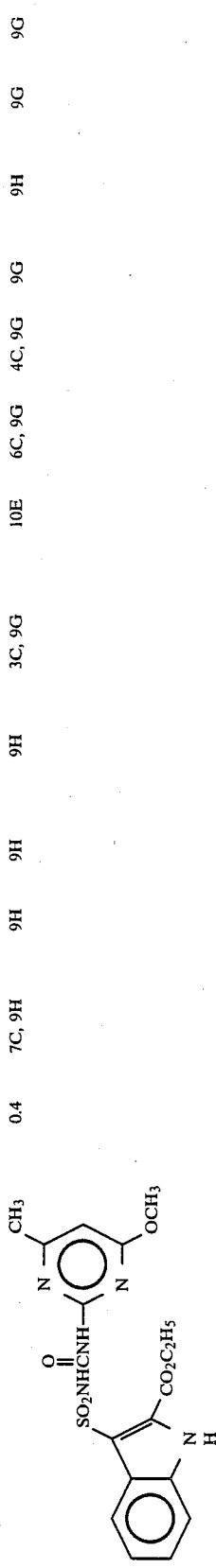 | 0.4 | 7C, 9H | 9H | 9H | 3C, 9G | 10E | 6C, 9G | 4C, 9G | 9G | 9H | 9G | 9G | | |
| 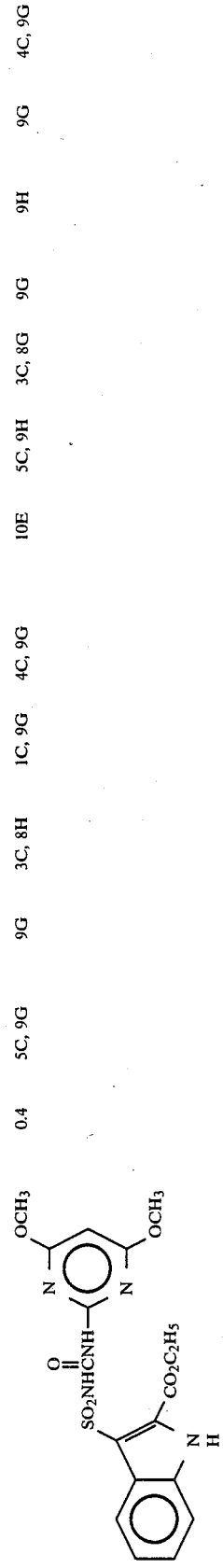 | 0.4 | 5C, 9H | 9G | 3C, 8H | 1C, 9G | 4C, 9G | 10E | 5C, 9H | 3C, 8G | 9G | 9H | 9G | 4C, 9G | |
| 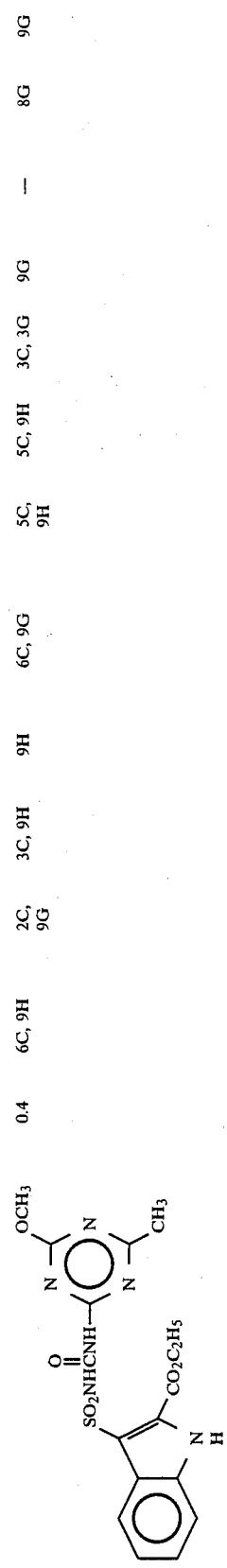 | 0.4 | 6C, 9H | 2C, 9G | 3C, 9H | 9H | 6C, 9G | 5C, 9H | 5C, 9H | 3C, 3G | 9G | — | 8G | 9G | |
| 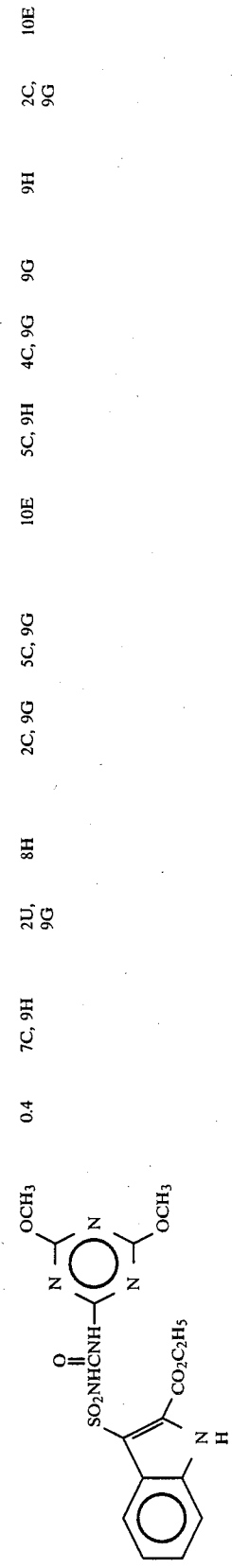 | 0.4 | 7C, 9H | 2U, 9G | 8H | 2C, 9G | 5C, 9G | 10E | 5C, 9H | 4C, 9G | 9G | 9H | 2C, 9G | 10E | |

TABLE A-continued

| Structure | | | | | | | | | | | | | |
|---|---|---|---|---|---|---|---|---|---|---|---|---|---|
| ![pyrimidine-sulfonylurea with indol-3-yl] | 0.4 | 2C | 3G | 3G | 1C | 1C | 5G | 6C | 0 | 5G | — | 2C | 0 |
| ![pyrimidine-sulfonylurea with 2-CO2C2H5, 5-ethylindol-3-yl] | 0.05 | 2C, 7G | 2C, 6G | 1H | 3G | 8G | 2C, 4G | 3G | 0 | 2H | — | 1C | 0 |
| ![pyrimidine-sulfonylurea with 2-CO2C2H5-indol-3-yl] | 0.05 | 2C, 9H | 1C, 9H | 2C, 7H | 1C, 9G | 3C, 9G | 5C, 9H | 4C, 8H | 1C, 6G | 1C, 4H | 9H | 4G | 4G, 1C |
| ![pyrimidine-sulfonylurea with 2-CO2C2H5, N-methylindol-3-yl] | 0.4 | 4G | 1C, 5G | 0 | 1C, 6G | 2C, 5G | 3G | 0 | 0 | 0 | — | 0 | 0 |

TEST B

Two plastic bulb pans were filled with fertilized and limed Fallsington silt loam soil. One pan was planted with corn, sorghum, Kentucky bluegrass and several grassy weeds. The other pan was planted with cotton, soybeans, purple nutsedge (*Cyperus rotundus*), and several broadleaf weeds. The following grassy and broadleaf weeds were planted: crabgrass (*Digitaria sanguinalis*), barnyardgrass (*Echinochloa crusgalli*), wild oats (*Avena fatua*), johnsongrass (*Sorghum halepense*), dallisgrass (*Paspalum dilatatum*), giant foxtail (*Setaria faberii*), cheatgrass (*Bromus secalinus*), mustard (*Brassica arvensis*), cocklebur (*Xanthium pensylvanicum*), pigweed (*Amaranthus retroflexus*), morningglory (*Ipomoea hederacea*), cassia (*Cassia tora*), teaweed (*Sida spinosa*), velvetleaf (*Abutilon theophrasti*), and jimsonweed (*Datura stramonium*). A 12.5 cm diameter plastic pot was also filled with prepared soil and planted with rice and wheat. Another 12.5 cm pot was planted with sugarbeets. The above four containers were treated pre-emergence with two of the test compounds within the scope of the invention.

Twenty-eight days after treatment, the plants were evaluated and visually rated for response to the chemical treatments utilizing the rating system described previously for Test A. The data are summarized in Table B. Note that the compounds are useful for weed control in crops such as soybeans, wheat and cotton.

TABLE B
PRE-EMERGENCE ON FALLSINGTON SILT LOAM

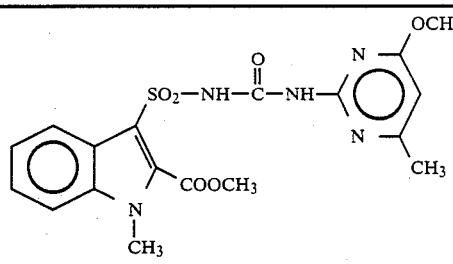

| Rate kg/ha | 0.03 | 0.12 |
|---|---|---|
| Crabgrass | 3G | 6G |
| Barnyardgrass | 3G | 7G,3H |
| Sorghum | 10C | 10C |
| Wild Oats | 7G, 3H | 7G, 5H |
| Johnsongrass | 4G, 2H | 6G, 5H |
| Dallisgrass | 0 | 4G |
| Giant foxtail | 3G | 5G, 3H |
| Ky. bluegrass | 7G, 5H | 8G, 5H |
| Cheatgrass | 5G, 3H | 8G, 8C |
| Sugarbeets | 7G, 3C | 7G, 7C |
| Corn | 4G, 4U | 6G, 5H |
| Mustard | 7G, 5C | 9G, 9C |
| Cocklebur | 6G, 3H | 8G, 5H |
| Pigweed | 5G | 10E |
| Nutsedge | 0 | 7G, 2C |
| Cotton | 0 | 3G |
| Morningglory | 0 | 2G |
| Cassia | 4G | 4G |
| Teaweed | 5G | 6G |
| Velvetleaf | 2G | 8G, 5H |
| Jimsonweed | 3G | 6G, 6C |
| Soybean | 0 | 3G |
| Rice | 6G, 5H | 8G, 8C |
| Wheat | 4G | 5G |

TABLE B-continued
PRE-EMERGENCE ON FALLSINGTON SILT LOAM

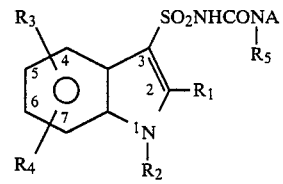

| Rate kg/ha | 0.03 | 0.12 |
|---|---|---|
| Crabgrass | 3G | 4G |
| Barnyardgrass | 6G | 8G, 3H |
| Sorghum | 8G, 5H | 10C |
| Wild Oats | 7G, 3H | 7G, 3H |
| Johnsongrass | 6G, 5H | 7G, 5H |
| Dallisgrass | 3G | 5G |
| Giant foxtail | 4G, 3H | 7G, 3H |
| Ky. bluegrass | 8G, 3H | 8G, 8C |
| Cheatgrass | 4G | 8G, 3H |
| Sugarbeets | 5G, 3C | 7G, 7C |
| Corn | 5G, 5H | 6G, 5H |
| Mustard | 7G, 8C | 7G, 7C |
| Cocklebur | 4G, 3H | 5G, 3H |
| Pigweed | 5G | 8G, 8C |
| Nutsedge | 0 | 3G |
| Cotton | 0 | 3G |
| Morningglory | 0 | 4G |
| Cassia | 0 | 3G |
| Teaweed | 6G, 2C | 7G, 2C |
| Velvetleaf | 5G, 5H | 7G, 5H |
| Jimsonweed | 3G | 6G, 2C |
| Soybean | 0 | 4G, 2C |
| Rice | 8G, 5H | 8G, 5H |
| Wheat | 2C | 3G, 3C |

I claim:
1. A compound selected from

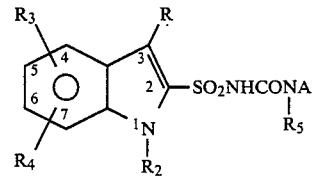

where
R is H, $C_1-C_4$ alkyl, $(CH_2)_mCO_2R_9$, $CH_2OC_2H_5$, $SO_2R_{10}$, CHO, $SO_2NR_{11}R_{12}-$, $CH_2N(CH_3)_2$ or $CH_2OCH_3$;

$R_1$ is H, $C_1-C_4$ alkyl, $CO_2R_6$, $C(O)NR_7R_8$, $C(O)R_{10}$, $SO_2R_{10}$, or $SO_2NR_{11}R_{12}$;

$R_2$ is H, $C_1-C_3$ alkyl or $SO_2C_6H_5$;

$R_3$ is H, F, Cl, Br, $C_1-C_3$ alkyl, $C_1-C_3$ alkoxy or $NO_2$;

$R_4$ is H, Cl or Br;

$R_5$ is H or $CH_3$;

$R_6$ is $C_1-C_4$ alkyl, $C_3-C_4$ alkenyl, $CH_2CH_2Cl$ or $CH_2CH_2OCH_3$;

$R_7$ and $R_8$ are independently H or $C_1$-$C_4$ alkyl, provided that the total number of carbon atoms is less than or equal to 4;

$R_9$ is H or $C_1$-$C_3$ alkyl $R_{10}$ is $C_1$-$C_3$ alkyl;

$R_{11}$ and $R_{12}$ are independently $C_1$-$C_3$ alkyl, provided that the total number of carbon atoms is less than or equal to 4.

m is 0, 1 or 2;

A is

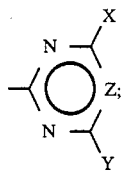

X is $CH_3$ or $OCH_3$;

Y is $CH_3$, $OCH_3$, $OC_2H_5$, $CH_2OCH_3$, Cl, H, $C_2H_5$ or $N(CH_3)_2$; and Z is N;

provided that (1) when $R_2$ is $SO_2C_6H_5$, then $R_1$ and R are H or $C_1$-$C_3$ alkyl; and (2) when m is 0, then $R_9$ is $C_1$-$C_3$ alkyl.

2. A compound of claim 1, Formula I where $R_1$ is H, $C_1$-$C_3$ alkyl, $CO_2R_6$, $C(O)NR_7R_8$, $SO_2NR_{11}R_{12}$ or $SO_2R_{10}$; and $R_5$ is H.

3. A compound of claim 2 where $R_3$ and $R_4$ are H.

4. A compound of claim 3 where $R_2$ is H or $CH_3$.

5. A compound of claim 4 where $R_1$ is H, $CO_2CH_3$, $SO_2CH_3$ or $SO_2N(CH_3)_2$.

6. A compound of claim 5 where Y is $CH_3$, $OCH_3$, $OC_2H_5$, $CH_2OCH_3$ or Cl.

7. A compound of claim 1, Formula II where R is H, $C_1$-$C_3$ alkyl, $(CH_2)_mCO_2R_9$, $SO_2R_{10}$ or $SO_2NR_{11}R_{12}$; and $R_5$ is H.

8. A compound of claim 7 where $R_3$ and $R_4$ are H.

9. A compound of claim 8 where $R_2$ is H or $CH_3$.

10. A compound of claim 9 where R is H, $CH_3$ or $(CH_2)_mCO_2$—($C_1$-$C_3$ alkyl).

11. A compound of claim 10 where Y is $CH_3$, $OCH_3$, $OC_2H_5$, or $CH_2OCH_3$.

12. The compound of claim 1, 3-[[(4,6-dimethoxy-1,3,5-triazin-2-yl) aminocarbonyl]aminosulfonyl]-1-methyl-1H-indole-2-carboxylic acid, methyl ester.

13. The compound of claim 1, 3-[[(4,6-dimethoxy-1,3,5-triazin-2-yl) aminocarbonyl]aminosulfonyl]-1-methyl-1H-indole-2-carboxylic acid, methyl ester.

14. The compound of claim 1, 3-[[(4-methyl-6-methoxy-1,3,5-triazin-2-yl) aminocarbonyl]-aminosulfonyl]-1-methyl-1H-indole-2-carboxylic acid, methyl ester.

15. The compound of claim 1, N-[(4,6-dimethoxy-1,3,5-triazin-2-yl) aminocarbonyl]-3-methyl-1H-indole-2-sulfonamide.

16. The compound of claim 1, N-[4,6-dimethoxy-1,3,5-triazin-2-yl) aminocarbonyl]-3-methyl-1H-indole-2-sulfonamide.

17. The compound of claim 1, N-[(4-methyl-6-methoxy-1,3,5-triazin-2-yl) aminocarbonyl]-3-methyl-1H-indole-2-sulfonamide.

18. The compound of claim 1, 3-[[(4,6-dimethoxy-1,3,5-triazin-2-yl) aminocarbonyl]-aminosulfonyl]-1H-indole-2-carboxylic acid, ethyl ester.

19. The compound of claim 1, 3-[[(4-methoxy-6-methyl-1,3,5-triazin-2-yl) aminocarbonyl]-aminosulfonyl]-1H-indole-2-carboxylic acid, ethyl ester.

20. A composition suitable for controlling the growth of undesired vegetation which comprises an effective amount of a compound of claim 1 and at least one of the following: surfactant, solid or liquid diluent.

21. A composition suitable for controlling the growth of undesired vegetation which comprises an effective amount of a compound of claim 2 and at least one of the following: surfactant, solid or liquid diluent.

22. A composition suitable for controlling the growth of undesired vegetation which comprises an effective amount of a compound of claim 3 and at least one of the following: surfactant, solid or liquid diluent.

23. A composition suitable for controlling the growth of undesired vegetation which comprises an effective amount of a compound of claim 4 and at least one of the following: surfactant, solid or liquid diluent.

24. A composition suitable for controlling the growth of undesired vegetation which comprises an effective amount of a compound of claim 5 and at least one of the following: surfactant, solid or liquid diluent.

25. A composition suitable for controlling the growth of undesired vegetation which comprises an effective amount of a compound of claim 6 and at least one of the following: surfactant, solid or liquid diluent.

26. A composition suitable for controlling the growth of undesired vegetation which comprises an effective amount of a compound of claim 7 and at least one of the following: surfactant, solid or liquid diluent.

27. A composition suitable for controlling the growth of undesired vegetation which comprises an effective amount of a compound of claim 8 and at least one of the following: surfactant, solid or liquid diluent.

28. A composition suitable for controlling the growth of undesired vegetation which comprises an effective amount of a compound of claim 9 and at least one of the following: surfactant, solid or liquid diluent.

29. A composition suitable for controlling the growth of undesired vegetation which comprises an effective amount of a compound of claim 10 and at least one of the following: surfactant, solid or liquid diluent.

30. A composition suitable for controlling the growth of undesired vegetation which comprises an effective amount of a compound of claim 11 and at least one of the following: surfactant, solid or liquid diluent.

31. A method for controlling the growth of undesired vegetation which comprises applying to the locus to be protected an effective amount of a compound of claim 1.

32. A method for controlling the growth of undesired vegetation which comprises applying to the locus to be protected an effective amount of a compound of claim 2.

33. A method for controlling the growth of undesired vegetation which comprises applying to the locus to be protected an effective amount of a compound of claim 3.

34. A method for controlling the growth of undesired vegetation which comprises applying to the locus to be protected an effective amount of a compound of claim 4.

35. A method for controlling the growth of undesired vegetation which comprises applying to the locus to be protected an effective amount of a compound of claim 5.

36. A method for controlling the growth of undesired vegetation which comprises applying to the locus to be protected an effective amount of a compound of claim 6.

37. A method for controlling the growth of undesired vegetation which comprises applying to the locus to be protected an effective amount of a compound of claim 7.

38. A method for controlling the growth of undesired vegetation which comprises applying to the locus to be protected an effective amount of a compound of claim 8.

39. A method for controlling the growth of undesired vegetation which comprises applying to the locus to be protected an effective amount of a compound of claim 9.

40. A method for controlling the growth of undesired vegetation which comprises applying to the locus to be protected an effective amount of a compound of claim 10.

41. A method for controlling the growth of undesired vegetation which comprises applying to the locus to be protected an effective amount of a compound of claim 11.

* * * * *